US011253634B2

(12) United States Patent
Savage et al.

(10) Patent No.: US 11,253,634 B2
(45) Date of Patent: Feb. 22, 2022

(54) CATIONIC STEROIDAL ANTIBIOTIC COMPOSITIONS FOR THE TREATMENT OF DERMAL TISSUE

(71) Applicants: Paul B. Savage, Mapleton, UT (US); Carl Genberg, Las Vegas, NV (US); Ronald Bracken, Monroe, GA (US)

(72) Inventors: Paul B. Savage, Mapleton, UT (US); Carl Genberg, Las Vegas, NV (US); Ronald Bracken, Monroe, GA (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 0 days.

(21) Appl. No.: 16/184,211

(22) Filed: Nov. 8, 2018

(65) Prior Publication Data

US 2019/0076581 A1     Mar. 14, 2019

Related U.S. Application Data

(63) Continuation of application No. 15/454,135, filed on Mar. 9, 2017, now Pat. No. 10,226,550.

(60) Provisional application No. 62/306,810, filed on Mar. 11, 2016, provisional application No. 62/412,079, filed on Oct. 24, 2016.

(51) Int. Cl.

| | |
|---|---|
| *A61L 27/54* | (2006.01) |
| *A61L 27/16* | (2006.01) |
| *A61L 27/18* | (2006.01) |
| *A61L 27/20* | (2006.01) |
| *A61L 27/24* | (2006.01) |
| *A61L 27/50* | (2006.01) |
| *A61L 24/00* | (2006.01) |
| *A61L 24/06* | (2006.01) |
| *A61L 24/08* | (2006.01) |
| *A61L 24/10* | (2006.01) |
| *A61L 26/00* | (2006.01) |
| *A61K 31/575* | (2006.01) |
| *A61L 24/04* | (2006.01) |
| *A61L 27/22* | (2006.01) |
| *A61L 27/58* | (2006.01) |

(52) U.S. Cl.
CPC .......... *A61L 27/54* (2013.01); *A61K 31/575* (2013.01); *A61L 24/0015* (2013.01); *A61L 24/046* (2013.01); *A61L 24/06* (2013.01); *A61L 24/08* (2013.01); *A61L 24/102* (2013.01); *A61L 26/0014* (2013.01); *A61L 26/0019* (2013.01); *A61L 26/0023* (2013.01); *A61L 26/0033* (2013.01); *A61L 26/0066* (2013.01); *A61L 27/16* (2013.01); *A61L 27/18* (2013.01); *A61L 27/20* (2013.01); *A61L 27/227* (2013.01); *A61L 27/24* (2013.01); *A61L 27/50* (2013.01); *A61L 27/58* (2013.01); *A61L 2300/216* (2013.01); *A61L 2300/404* (2013.01); *A61L 2300/41* (2013.01); *A61L 2400/06* (2013.01); *A61L 2430/34* (2013.01); *A61L 2430/36* (2013.01)

(58) Field of Classification Search
CPC .......... A61L 27/54; A61L 27/16; A61L 27/18; A61L 27/20; A61L 27/24; A61L 27/50; A61L 24/0015; A61L 24/06; A61L 24/102; A61L 26/0014; A61L 26/0019; A61L 26/0023; A61L 26/0033; A61L 26/0066; A61L 24/046; A61L 27/227; A61L 27/58; A61L 2300/216; A61L 2400/06; A61L 2430/36; A61L 2300/404; A61L 2300/41; A61L 2430/34; A61L 24/001; A61L 24/043; A61L 26/0052; A61L 27/26; A61L 27/20; A61L 24/06; A61L 24/08; A61L 26/0019; A61L 2300/404; A61K 31/575; A61K 9/0019; A61K 31/10; A61P 17/02; A61P 31/00
See application file for complete search history.

(56) References Cited

U.S. PATENT DOCUMENTS

| | | | |
|---|---|---|---|
| 821,187 | A | 5/1906 | Peters |
| 3,843,779 | A | 10/1974 | Norfleet |
| 4,248,236 | A | 2/1981 | Linder |

(Continued)

FOREIGN PATENT DOCUMENTS

| | | |
|---|---|---|
| CA | 2322847 A1 | 9/1999 |
| CA | 2842460 A1 | 1/2013 |

(Continued)

OTHER PUBLICATIONS

U.S. Appl. No. 13/783,007, filed Mar. 1, 2013, Savage.

(Continued)

*Primary Examiner* — Quanglong N Truong
(74) *Attorney, Agent, or Firm* — Workman Nydegger

(57) ABSTRACT

This disclosure relates to dermal treatment compositions, such as dermal fillers and tissue glues, and injectable compositions that incorporate one or more cationic steroidal antimicrobials (CSAs). The CSAs are incorporated into the dermal treatment compositions to provide effective antimicrobial, anti-inflammatory, analgesic, anti-swelling and/or tissue-healing properties. A treatment composition includes a component formed from a biologically compatible material suitable for injection into and/or application onto tissue at a treatment site. One or more CSA compounds are mixed with the biologically compatible material so that the one or more CSA compounds are incorporated within the composition, forming a reservoir of CSA compounds within the resulting bolus of the treatment composition after injection and/or application.

20 Claims, 14 Drawing Sheets

(56) References Cited

U.S. PATENT DOCUMENTS

| | | |
|---|---|---|
| 4,284,236 A | 8/1981 | Bradshaw |
| 4,289,755 A | 9/1981 | Dhabhar |
| 4,296,206 A | 10/1981 | Simons |
| 4,473,988 A | 10/1984 | Scott |
| 4,661,341 A | 4/1987 | Benedict et al. |
| 4,723,950 A | 2/1988 | Lee |
| 4,765,855 A | 8/1988 | Geoffroy-Dechaume et al. |
| 4,842,593 A | 6/1989 | Jordan et al. |
| 4,865,855 A | 9/1989 | Hansen et al. |
| 4,972,848 A | 11/1990 | Di Domenico |
| 5,025,754 A | 6/1991 | Plyler |
| 5,286,479 A | 2/1994 | Garlich et al. |
| 5,310,545 A | 5/1994 | Eisen |
| 5,352,682 A | 10/1994 | Sipos |
| 5,356,630 A | 10/1994 | Laurencin et al. |
| 5,364,650 A | 11/1994 | Guthery |
| 5,380,839 A | 1/1995 | McCall et al. |
| 5,552,057 A | 9/1996 | Hughes et al. |
| 5,624,704 A | 4/1997 | Darouiche et al. |
| 5,687,714 A | 11/1997 | Kolobow |
| 5,721,359 A | 2/1998 | Dunn et al. |
| 5,763,430 A | 6/1998 | Zasloff |
| 5,919,183 A | 7/1999 | Field |
| 6,117,332 A | 9/2000 | Hatch et al. |
| 6,217,896 B1 | 4/2001 | Benjamin |
| 6,228,393 B1 | 5/2001 | DiCosmo et al. |
| 6,329,488 B1 | 12/2001 | Terry et al. |
| 6,344,184 B1 | 2/2002 | Rolla |
| 6,350,738 B1 | 2/2002 | Savage et al. |
| 6,486,148 B2 | 11/2002 | Savage et al. |
| 6,562,318 B1 | 5/2003 | Filler |
| 6,582,713 B2 | 6/2003 | Newell et al. |
| 6,673,771 B1 | 1/2004 | Greene et al. |
| 6,767,904 B2 | 7/2004 | Savage et al. |
| 6,803,030 B2 | 10/2004 | De et al. |
| 6,803,066 B2 | 10/2004 | Traeder |
| 6,872,303 B2 | 3/2005 | Knapp et al. |
| 6,872,306 B2 | 3/2005 | Shen |
| 6,939,376 B2 | 7/2005 | Shulze et al. |
| 7,226,577 B2 | 6/2007 | Cappelletti et al. |
| 7,235,552 B1 | 6/2007 | Hesse et al. |
| 7,282,214 B2 | 10/2007 | Willcox et al. |
| 7,381,439 B2 | 6/2008 | Hilgren et al. |
| 7,481,973 B2 | 1/2009 | Beilfuss et al. |
| 7,598,234 B2 | 10/2009 | Savage et al. |
| 7,611,692 B2 | 11/2009 | Cappelletti et al. |
| 7,659,061 B2 | 2/2010 | Hendl et al. |
| 7,754,705 B2 | 7/2010 | Savage et al. |
| 7,850,947 B2 | 12/2010 | Cappelletti et al. |
| 7,854,941 B2 | 12/2010 | Urban et al. |
| 7,993,903 B2 | 8/2011 | Hayakawa et al. |
| 7,999,390 B2 | 8/2011 | Ishigaki et al. |
| 8,211,879 B2 | 7/2012 | Savage et al. |
| 8,420,050 B2 | 4/2013 | Cappelletti et al. |
| 8,444,954 B2 | 5/2013 | Cappelletti et al. |
| 8,529,681 B1 | 9/2013 | Hibbs et al. |
| 8,530,002 B1 | 9/2013 | Hibbs et al. |
| 8,557,031 B1 | 10/2013 | Hibbs et al. |
| 8,623,416 B2 | 1/2014 | Zasloff et al. |
| 8,691,252 B2 | 4/2014 | Savage |
| 8,784,857 B2 | 7/2014 | Savage |
| 8,787,857 B2 | 7/2014 | Ezaki |
| 8,932,614 B2 | 1/2015 | Savage et al. |
| 8,945,217 B2 | 2/2015 | Savage et al. |
| 8,975,310 B2 | 3/2015 | Savage |
| 9,155,746 B2 | 10/2015 | Genberg et al. |
| 9,161,942 B2 | 10/2015 | Genberg et al. |
| 9,314,472 B2 | 4/2016 | Beus et al. |
| 9,345,655 B2 | 5/2016 | Vazquez et al. |
| 9,387,215 B2 | 7/2016 | Beus et al. |
| 9,434,759 B1 | 9/2016 | Savage |
| 9,527,883 B2 | 12/2016 | Savage et al. |
| 9,533,063 B1 | 1/2017 | Savage |
| 2002/0091278 A1 | 7/2002 | Savage et al. |
| 2002/0091433 A1 | 7/2002 | Ding et al. |
| 2003/0018306 A1 | 1/2003 | Bucay-Couto et al. |
| 2003/0099717 A1 | 5/2003 | Cabrera |
| 2003/0170354 A1 | 9/2003 | Beelman et al. |
| 2003/0232791 A1 | 12/2003 | Levitt et al. |
| 2004/0009227 A1 | 1/2004 | Yao |
| 2004/0011358 A1 | 1/2004 | Smaldone et al. |
| 2004/0018154 A1 | 1/2004 | Pan |
| 2004/0058974 A1 | 3/2004 | Courtney et al. |
| 2004/0071781 A1 | 4/2004 | Chattopadhyay et al. |
| 2004/0126409 A1 | 7/2004 | Wilcox et al. |
| 2004/0134292 A1 | 7/2004 | Roth |
| 2004/0170563 A1 | 9/2004 | Meade |
| 2004/0259445 A1 | 12/2004 | Hilfenhaus et al. |
| 2005/0032765 A1 | 2/2005 | Savage et al. |
| 2005/0075321 A1 | 4/2005 | Ahlem et al. |
| 2005/0244468 A1 | 11/2005 | Huang et al. |
| 2005/0267051 A1 | 12/2005 | Lee et al. |
| 2006/0014738 A1 | 1/2006 | Wachendorff-neumann et al. |
| 2006/0062742 A1 | 3/2006 | Davis et al. |
| 2006/0269485 A1 | 11/2006 | Friedman et al. |
| 2007/0053788 A1 | 3/2007 | Zhao |
| 2007/0077292 A1 | 4/2007 | Pinsky |
| 2007/0106393 A1 | 5/2007 | Miles et al. |
| 2007/0134292 A1 | 6/2007 | Suokas et al. |
| 2007/0170563 A1 | 7/2007 | Chen |
| 2007/0190066 A1 | 8/2007 | Savage et al. |
| 2007/0190067 A1 | 8/2007 | Savage et al. |
| 2007/0190558 A1 | 8/2007 | Savage et al. |
| 2007/0243225 A1 | 10/2007 | Mckay |
| 2007/0269375 A1 | 11/2007 | Chen et al. |
| 2008/0085949 A1 | 4/2008 | Mcghee |
| 2008/0124376 A1 | 5/2008 | Pruitt et al. |
| 2008/0174035 A1 | 7/2008 | Winterton |
| 2008/0188819 A1 | 8/2008 | Kloke et al. |
| 2008/0279944 A1 | 11/2008 | Sawhney |
| 2009/0016973 A1 | 1/2009 | Ratcliff et al. |
| 2009/0024101 A1 | 1/2009 | Toshishige et al. |
| 2009/0054295 A1 | 2/2009 | Vicari et al. |
| 2009/0068122 A1 | 3/2009 | Pilch et al. |
| 2009/0099531 A1 | 4/2009 | Griesbach, III |
| 2009/0226884 A1 | 9/2009 | Tsujimoto et al. |
| 2009/0252781 A1 | 10/2009 | Sawhney et al. |
| 2009/0279944 A1 | 11/2009 | Schmitz et al. |
| 2009/0324517 A1 | 12/2009 | Kline |
| 2010/0022481 A1 | 1/2010 | Wang et al. |
| 2010/0092398 A1 | 4/2010 | Reynolds |
| 2010/0226884 A1 | 9/2010 | Chang et al. |
| 2010/0310478 A1 | 12/2010 | Fitzgerald et al. |
| 2010/0330086 A1 | 12/2010 | Savage et al. |
| 2011/0033540 A1* | 2/2011 | Daniloff .................. A61L 27/52<br>424/484 |
| 2011/0091376 A1 | 4/2011 | Savage et al. |
| 2011/0123624 A1 | 5/2011 | Zasloff |
| 2011/0135742 A1* | 6/2011 | Kim .................... A61K 9/0014<br>424/499 |
| 2011/0171144 A1 | 7/2011 | Wang et al. |
| 2011/0230589 A1 | 9/2011 | Maggio et al. |
| 2012/0088733 A1 | 4/2012 | Kim et al. |
| 2012/0107382 A1 | 5/2012 | Savage et al. |
| 2012/0128793 A1 | 5/2012 | Miller et al. |
| 2013/0004586 A1 | 1/2013 | Vachon |
| 2013/0022651 A1 | 1/2013 | Savage |
| 2013/0034500 A1 | 2/2013 | Savage et al. |
| 2013/0040265 A1 | 2/2013 | Park et al. |
| 2013/0089580 A1* | 4/2013 | Boutros .................. A61L 27/16<br>424/400 |
| 2013/0137668 A1 | 5/2013 | Fein et al. |
| 2013/0234842 A1 | 9/2013 | Leitz |
| 2013/0236619 A1 | 9/2013 | Savage |
| 2013/0243823 A1 | 9/2013 | Genberg et al. |
| 2013/0243842 A1 | 9/2013 | Genberg et al. |
| 2013/0280312 A1 | 10/2013 | De Szalay |
| 2013/0280391 A1 | 10/2013 | Savage |
| 2014/0062960 A1 | 3/2014 | Kim et al. |
| 2014/0194401 A1 | 7/2014 | Genberg et al. |
| 2014/0219914 A1 | 8/2014 | Govindan et al. |
| 2014/0228905 A1 | 8/2014 | Bolea |
| 2014/0271761 A1 | 9/2014 | Savage et al. |
| 2014/0274913 A1 | 9/2014 | Savage et al. |

(56) References Cited

U.S. PATENT DOCUMENTS

| | | |
|---|---|---|
| 2014/0305461 A1 | 10/2014 | Pimenta et al. |
| 2014/0336131 A1 | 11/2014 | Savage et al. |
| 2014/0363780 A1 | 12/2014 | Vazquez et al. |
| 2015/0093423 A1 | 4/2015 | Savage et al. |
| 2015/0110767 A1 | 4/2015 | Savage et al. |
| 2015/0140063 A1 | 5/2015 | Savage |
| 2015/0203257 A1 | 7/2015 | Canegallo |
| 2015/0203527 A1 | 7/2015 | Savage |
| 2015/0239928 A1 | 8/2015 | Savage |
| 2015/0258121 A1 | 9/2015 | Darien et al. |
| 2015/0258122 A1 | 9/2015 | Beus et al. |
| 2015/0258123 A1 | 9/2015 | Savage et al. |
| 2015/0314342 A1 | 11/2015 | Beus et al. |
| 2015/0366880 A1 | 12/2015 | Genberg et al. |
| 2015/0374719 A1 | 12/2015 | Genberg et al. |
| 2015/0374720 A1 | 12/2015 | Genberg et al. |
| 2016/0022702 A1 | 1/2016 | Savage et al. |
| 2016/0045421 A1 | 2/2016 | Vazquez et al. |
| 2016/0052959 A1 | 2/2016 | Savage |
| 2016/0096864 A1 | 4/2016 | Savage |
| 2016/0193232 A1 | 7/2016 | Beus et al. |
| 2016/0199390 A1 | 7/2016 | Beus et al. |
| 2016/0311850 A1 | 10/2016 | Savage et al. |
| 2016/0311851 A1 | 10/2016 | Savage et al. |
| 2017/0035677 A1 | 2/2017 | Vazquez et al. |
| 2017/0080128 A1 | 3/2017 | Genberg et al. |
| 2017/0137459 A1 | 5/2017 | Savage |
| 2017/0210776 A1 | 7/2017 | Savage |
| 2017/0232004 A1 | 8/2017 | Savage et al. |
| 2017/0258963 A1 | 9/2017 | Savage et al. |
| 2018/0164221 A1 | 6/2018 | Singh et al. |
| 2018/0280550 A1 | 10/2018 | Savage |
| 2019/0076581 A1 | 3/2019 | Savage et al. |

FOREIGN PATENT DOCUMENTS

| | | | |
|---|---|---|---|
| CA | 2741177 C | * 3/2018 | ............. A61L 31/06 |
| CN | 1236322 A | 11/1999 | |
| CN | 101247838 A | 8/2008 | |
| CN | 101378761 | 3/2009 | |
| CN | 102145005 | 8/2011 | |
| CN | 102172356 | 9/2011 | |
| CN | 104039369 A | 9/2014 | |
| DE | 1037074 | 8/1958 | |
| EP | 0341951 | 11/1989 | |
| EP | 1208844 | 5/2002 | |
| EP | 1219631 | 7/2002 | |
| EP | 1058552 B1 | 6/2004 | |
| EP | 1311531 B1 | 5/2016 | |
| JP | 60-080457 A | 5/1985 | |
| JP | 02014741 | 1/1990 | |
| JP | H0474026 | 11/1992 | |
| JP | 06153779 | 6/1994 | |
| JP | 07501826 | 2/1995 | |
| JP | 09248454 | 9/1997 | |
| JP | 2002505292 | 2/2002 | |
| JP | 2002255771 | 9/2002 | |
| JP | 2002534532 | 10/2002 | |
| JP | 2002538093 | 11/2002 | |
| JP | 2004-506599 A | 3/2004 | |
| JP | 2004506645 | 3/2004 | |
| JP | 2009-131625 A | 6/2009 | |
| JP | 2010-059194 A | 3/2010 | |
| JP | 2010533051 | 10/2010 | |
| JP | 2010538074 | 12/2010 | |
| JP | 2011527702 | 11/2011 | |
| JP | 2014500741 | 1/2014 | |
| JP | 2014-520900 A | 8/2014 | |
| JP | 2014-530191 A | 11/2014 | |
| WO | WO 1995024415 | 9/1995 | |
| WO | 98/05337 A1 | 2/1998 | |
| WO | WO 9827106 | 6/1998 | |
| WO | 99/45024 A1 | 9/1999 | |
| WO | WO 1999044616 | 9/1999 | |
| WO | WO 2000042058 | 7/2000 | |
| WO | WO 2002014342 | 2/2002 | |
| WO | WO2002067979 | 9/2002 | |
| WO | WO2003015757 | 2/2003 | |
| WO | 03/66119 | 8/2003 | |
| WO | WO03090799 | 11/2003 | |
| WO | WO2004082588 | 9/2004 | |
| WO | WO 2004112852 | 12/2004 | |
| WO | WO 2007089903 | 8/2007 | |
| WO | WO 2007089906 | 8/2007 | |
| WO | WO 2007089907 | 8/2007 | |
| WO | WO 2007134176 | 11/2007 | |
| WO | 2008/048340 A2 | 4/2008 | |
| WO | WO2008096149 | 8/2008 | |
| WO | WO 2008038965 | 4/2009 | |
| WO | WO2009049370 | 4/2009 | |
| WO | WO 2009079066 | 6/2009 | |
| WO | WO2009144708 | 12/2009 | |
| WO | WO2010006192 | 1/2010 | |
| WO | WO2010036427 | 4/2010 | |
| WO | WO2010062562 | 6/2011 | |
| WO | WO2011066260 | 6/2011 | |
| WO | WO2011109704 | 9/2011 | |
| WO | WO2012061651 | 5/2012 | |
| WO | 2013/013221 A1 | 1/2013 | |
| WO | 2013/013223 A1 | 1/2013 | |
| WO | WO2013029055 | 2/2013 | |
| WO | WO2013029059 | 2/2013 | |
| WO | 2013/040265 A1 | 3/2013 | |
| WO | WO2013040269 | 3/2013 | |
| WO | WO2013131060 | 6/2013 | |
| WO | WO 2013109236 | 7/2013 | |
| WO | WO 2013167743 | 11/2013 | |
| WO | WO 2014062960 | 4/2014 | |
| WO | 2014/107740 A2 | 7/2014 | |
| WO | WO 2014151411 | 9/2014 | |
| WO | WO2015058087 | 4/2015 | |
| WO | 2015/138716 A2 | 9/2015 | |
| WO | WO2015200815 | 12/2015 | |
| WO | WO2016172543 | 10/2016 | |
| WO | WO2016186821 | 11/2016 | |
| WO | 2017/053355 A1 | 3/2017 | |

OTHER PUBLICATIONS

U.S. Appl. No. 14/866,213, filed Sep. 25, 2015, Savage.
U.S. Appl. No. 15/076,313, filed Mar. 21, 2016, Beus et al.
U.S. Appl. No. 15/135,969, filed Apr. 22, 2016, Savage et al.
U.S. Appl. No. 15/135,900, filed Apr. 22, 2016, Savage et al.
U.S. Appl. No. 15/934,534, filed Mar. 2018, Savage, Paul B.
U.S. Appl. No. 15/895,848, filed Feb. 2018, Genberg, et al.
U.S. Appl. No. 15/926,534, filed Mar. 2018, Savage.
U.S. Appl. No. 15/926,577, filed Mar. 2018, Savage et al.
U.S. Appl. No. 16/184,211, filed Nov. 2018, Savage.
Alafort et al., "Lys and Arg in UBI: A specific site for a stable Tc-99m complex?", Nuclear Medicine and Biology 30 (2003) 605-615.
Alhanout K et al: "Squalamine as an example of a new potent antimicrobial agents class: a critical review.", Current Medicinal Chemistry 2010, vol. 17, No. 32, 2010, pp. 3909-3917.
Atiq-Ur-Rehman Li C et al: "Preparation of Amino Acid-Appended Cholic Acid Derivatives as Sensitizers of Gram-Negative Bacteria", Tetrahedron Letters, Elsevier, Amsterdam, NL, vol. 40, No. 10, Mar. 5, 1999 (Mar. 5, 1999), pp. 1865-1868, XP004155984, ISSN: 0040-4039, DOI: 10.1016/S0040-4039(99)00075-1.
Bellini et al., "Cholic and deoxycholic acids derivatives (Part I). Antimicrobial activity of cholane compounds", European J. of Medicinal Chem., 18(2), pp. 185-190, 1983.
Bellini et al., "Cholic and deoxycholic acids derivatives (Part II). Antimicrobial activity of cholane compounds", European J. of Medicinal Chem., 18(2), pp. 191-195, 1983.
Berge et al., "Pharmaceutical Salts", Journal of Pharmaceutical Sciences, Jan. 1977, vol. 66, No. 1, pp. 1-19.
Bridot et al., "Hybrid Gadolinium Oxide Nanoparticles: Multimodal Contrast Agents for in Vivo Imaging", Journal of American Chemical Society, vol. 129, No. 16, pp. 5076-5084, Mar. 31, 2007.

(56) References Cited

OTHER PUBLICATIONS

Britton et al, "Imaging bacterial infection with 99mTc-ciprofloxacin (Infection)", Journal of Clinical Pathology, vol. 55, pp. 817-823, Apr. 6, 2015

Brown, "Bioisosteres in Medicinal Chemistry, First Edition", edited by Nathan Brown, 2012, Ch. 2 Classical Bioisosteres, pp. 1-52

Bucki et al., "Resistance of the antibacterial agent ceragenin CSA-13 to inactivation by DNA or F-actin and its activity in cystic fibrosis sputum", Journal of Antimicrobial Chemotherapy (2007) 60: 535-545, 11 pages.

Bucki et al., "Salivary mucins inhibit antibacterial activity of the cathelicidin-derived LL-37 peptide but not the cationic steroid CSA-13", Journal of Antimicrobial Chemotherapy (2008) 62: 329-335, 7 pages.

Chin et al, "Antimicrobial Activities of Ceragenins against Clinical Isolates of Resistant *Staphylococcus aureus*", Antimicrobial Agents and Chemotherapy, vol. 51, No. 4, Apr. 2007, p. 1268-1273.

Clara et al., "Preclinical evaluation of magainin-A as a contraceptive antimicrobial agent", Fertility and Sterility 81 (5), pp. 1357-1365, 2004.

Dörwald, "Side reactions in organic synthesis", 2005, Wiley-VCH Verlag GmbH & co., KGAA Weinhelm, Preface. p. IX.

Epand et al., "Bacterial lipid composition and the antimicrobial efficacy of cationic steroid compounds (Ceragenins)", BBA, 2007, pp. 65-78.

Fichna et al., "Synthesis of Target-Specific Radiolabeled Peptides for Diagnostic Imaging", Bioconjugate Chem., 2003, 14, 3-17, American Chemical Society.

Fritsch et al, "In Vitro Activity of Nine Developmental Cationic Steroid Compounds (Ceragenins) against Clinical Isolates of Clostridium difficile", The 46th Interscience Conference on Antimicrobial Agents and Chemotherapy, Sep. 27, 2006, pp. 1-1.

Guan et al: "Preparation and Characterization of Cholic Acid-Derived Antimicrobial Agents with Controlled Stabilities", Organic Letters, American Chemical Society, US, vol. 2, No. 18, Sep. 7, 2000 (Sep. 7, 2000), pp. 2837-2840.

Guan et al: "Supporting Information: Preparation and Characterization of Cholic Acid-Derived Antimicrobial Agents with Controlled Stabilities", Organic Letters, Aug. 17, 2000 (Aug. 17, 2000), pp. 1-7, XP55017313, Retrieved from the Internet: URL:http://pubs.acs.org/doi/suppl/10.1021/010062704/suppl file/o10062704 sl.pdf.

Howell et al., "Ceragenins: A 1-18, class of Antiviral Compounds to Treat Orthopox Infections", Journal of Investigative Dermatology, vol. 129, No. 11, Jun. 11, 2009, pp. 2688-2675.

Isogai E et al: "Ceragenin CSA-13 exhibits antimicrobial activity against cariogenic and periodontopathic bacteria", Oral Microbiology and Immunology, vol. 24, No. 2, Apr. 2009 (Apr. 2009), pp. 170-172.

International Search Report for PCT Application No. PCT/US2009/047485 dated Feb. 17, 2010.

International Search Report for PCT Application No. PCT/US2011/059225 dated Jan. 31, 2012.

International Search Report for PCT Application No. PCT/US2012/047750, dated Oct. 5, 2012.

International Search Report for PCT Application No. PCT/US2012/055244 dated Dec. 5, 2012.

International Search Report for PCT Application No. PCT/US2012/055248 dated Feb. 14, 2013.

International Search Report for PCT Application No. PCT/US2013/038090, dated Jul. 24, 2013.

International Search Report for PCT Application No. PCT/US2014/034986 dated Aug. 28, 2014.

International Search Report for PCT Application No. PCT/US2013/065510 dated Apr. 30, 2015.

International Search Report for PCT Application No. PCT/US2015/020166 dated Sep. 2, 2015.

International Search Report for PCT Application No. PCT/US2015/038029 dated Sep. 29, 2015.

International Search Report for PCT Application No. PCT/US2015/046412 dated Dec. 1, 2015.

International Search Report for PCT Application No. PCT/US2015/054434 dated Dec. 23, 2015.

Iuliano, "Synthesis of four cholic acid-based CSPs containing 2-naphthyl carbamate and 3,5-dinitrophenylcarbamate moieties and their evaluation in the HPLC resolution of racemic compounds", Tetrahedron: Asymmetry 13 (2002) 1265-1275.

Lai, et al., "Controlled Released of a Bactericidal Ceragenin-Polymer Conjugate", Sep. 27, 2006, p. 1, 46th Annual Interscience Conference on Antimicrobial Agents and Chemotherapy.

Lankinen et al., "Ga-Dota-Peptide Targeting VAP-1 for In Vivo Evaluation of Inflammatory and Infectious Bone Conditions", 52nd Annual Meeting of the Orthopaedic Research Society.

Leszczynska et al., "Potential of ceragenin CSA-13 and its mixture with pluronic F-127 as treatment of topical bacterial infections", Journal of Applied Microbiology, vol. 110, No. 1, Oct. 21, 2010, pp. 229-238.

Li, et al., "Antimicrobial Activities of Amine- and Guanidine-functionalized Cholic Acid Derivatives", Antimicrobial Agents and Chemotherapy, American Society for Microbiology, Washington DC, US, vol. 43, No. 6, Jun. 1999, pp. 1347-1349.

Li et al., "Incremental conversion of Outer-Membrane Permeabilizers into Potent Antibiotics for Gram-Negative Bacteria", J. Am. Chem. Soc. 1999, 121, 931-940.

Lowe et al., "Effect of Hydrophobicity of a Drug on its Release from Hydrogels with Different Topological Structures" Journal of Polymer Science (1999) 73: 1031-1039 (9 pages).

Massoud et al., "Molecular imaging in living subjects: seeing fundamental biological processes in a new light", Genes & Development 17: 545-580 2003, Cold Spring Harbor Laboratory Press.

Muñoz-Juárez et al., "Wide-Lumen Stapled Anastomosis vs. Conventional End-to-End Anastomosis in the Treatment of Crohn's Disease", Dis Colon Rectum 2001; 44: No. 1, 20-26).

Perry et al., "Assessing peri-implant tissue infection prevention in a percutaneous model", Journal of Biomedical Materials Research Part B: Applied Biomaterials, vol. 02B, Nov. 19, 2009, pp. 397-408.

Pitten F-A, et al., "Efficacy of Cetylpyridinium Chloride Used as Oropharyngeal Antiseptic" Arzenimittel Forschung. Drug Research, ECV Editio Cantor Verlag, Aulendorf, DE, vol. 51, No. 7, Jan. 1, 2001, pp. 588-595.

Roohi et al., Prepration, quality control and biological evaluation of 99m-Tc-labelled cationic steroid antibiotic (CSA-13), Radiochim. Acta 197, 57-62 (2009).

Savage, et al., "Antibacterial Activities of Thin Films Containing Ceragenins", Microbial Surfaces: Structure, Interactions and Reactivity, ACS, May 30, 2008, pp. 65-78.

Paul B. Savage, et al: "Antibacterial Properties of cationic steroid antibiotics", FEMS Microbiology Letters, vol. 217, Nov. 2002, pp. 1-7.

Savage et al, "Thin Films Containing Ceragenins Prevent Biofilm Formation on Endotracheal Tubes", 9th International Federation of Infection Control Congress, Oct. 14, 2008, pp. 1-1.

P. B. Savage, et al., "Use of a Ceragenin-Based Coating to Prevent Bacterial Colonization of Urinary Catheters", 48th Annual Interscience Conference on Anti-Microbial Agents & Chemotherapy, Oct. 26, 2008, pp. 1-1.

Schmidmaier et al., "Local Application of Growth Factors (Insulin-Like Growth Factor-1 and Transforming Growth Factor-β1) From a Biodegradable Poly(D, L-lactide) Coating of Osteosynthetic Implants Accelerates Fracture Healing in Rats", Bone vol. 28 No. 4, Apr. 2001.

Shi et al., "Multi-center randomized double-blind clinical trial on efficacy of a mouthwash containing 0.1% cetylpiridinium chloride on gingivitis and plaque and its safety", Chinese Journal of Evidence-Based Medicine (Sep. 2003, vol. 3, No. 3, pp. 171-177).

Sinclair et al., "Development of a broad spectrum polymer-released antimicrobial coating for the prevention of resistant strain bacterial infections", Journal of Biomedical Materials Research Part A, vol. 100A, No. 10, May 24, 2012, pp. 2732-2738.

Steeneveld et al., "Cow-specific treatment of clinical mastitis: an economic approach", Journal of Dairy Science vol. 94, Jan. 2011, pp. 174-188.

Suzuki et al., "Molecular Genetics of Plant Sterol Backbone Synthesis", 2007; Lipids; 42: 47-54.

(56) References Cited

OTHER PUBLICATIONS

Van Bambeke et al: "The bacterial envelope as a target for novel anti-MRSA antibiotics", Trends in Pharmacological Sciences, Elsevier, Haywarth, GB, vol. 29, No. 3, Feb. 11, 2008 (Feb. 11, 2008), pp. 124-134.
Van Den Bogaard et al., "Antibiotic Usage in Animals: Impact on Bacterial Resistance and Public Health"; 1999; Drugs; 58 (4): 589-607.
Welling et al., "Radiochemical and biological characteristics of 99m-Tc-UBI 29-41 for imaging of bacterial infections", Nuclear Medicine and Biology 29 (2002) 413-422.
Williams et al., "In vivo efficacy of a silicone-cationic steroid antimicrobial coating to prevent implant-related infection", Biomaterials, Nov. 2012: 33(33): 8641-8656 (Department of Brigham Young University).
Wu et al., "Biodegradable hydrophobic-hydrophilic hybrid hydrogels: swelling behavior and controlled drug release", Journal of Biomaterials Science Polymer Edition (J. Biomatter. Sci. Polymer Ed.) (2008) 19 (4): 411-429 (20 pages, including copyright information).
Xin-Zhong Lai et al., "Ceragenins: Cholic Acid-Based Mimics of Antimicrobial peptides", Account of Chemical Research vol. 41, No. 10, Oct. 21, 2008, pp. 1233-1240.
Yin, et al., "Antiangiogenic Treatment Delays Chondrocyte Maturation and Cone Formation During Lim Skeletogenesis", Journal of Bone and Mineral Research, American Society for Bone and Mineral Research, New York, NY, US, vol. 17, No. 1, Jan. 1, 2002.
Zanger et al., "Structure-Activity Relationship and Drug Design", Remington's Pharmaceutical Sciences, Chapter 27, 16th Edition, 1980, pp. 420-425.
BASF, Pluronic® Block Copolymer NF Grades (Poloxamer NF Grades), Technical Bulletive (2004).
Belikov V.G., Pharmaceutical Chemistry, M., Higher School, 1993, p. 43-47.
Bush, "Staphylococcal Infections", Merck Manuals Professional Edition, http://www.merckmanuals.com/professional/infectious-diseases/gram-positive-cocci/staphylococcal-infections.
Cipolla et al., "Inhaled antibiotics to treat lung infection", Pharm Pat Anal., Sep. 2013.
Dennison et al., "Anticancer α-Helical Peptides and Structure/Function Relationships Underpinning their Interactions with Tumour Cell Membranes", Current Protein and Peptide Science, 2006, 7, No. 6, pp. 1-13.
Derakhshandeh et al., "Thermosensitive Pluronic hydrogel: prolonged injectable formulation for drug abuse", Drug Design, Development and Therapy, 2010, 255-262.
Elder et al., "The Utility of Sulfonate Salts in Drug Development", Journal of Pharmaceutical Sciences 99(7): 2948-2961.
Erskine et al., "Mastitis in Cattle", Merck Manual: Veterinary Manual. Electronic Resource: [http://www.merckvetmanual.com/reproductive-system/mastitis-in-large-animals/mastitis-in-cattle], retrieved Mar. 8, 2017.
Food definition, Merriam Webster, https://www.merriam-webster.com/dictionary/food, Accessed Feb. 12, 2018.
Huang L. et al.: "Synthesis and characterization of organometallic rhenium(I) and technetium(I) bile acid complexes" Journal of organometallic chemistry, Elsevier-Sequoia S.A. Lausanne, CH, col. 694, No. 20, Sep. 15, 2009, pp. 3247-3253.
International Search Report for PCT Application No. PCT/US2018/023566 dated Mar. 21, 2018.
Jones et al, "Physicochemical Characterization of Hexetidine-Impregnated Endotracheal Tube Poly(Vinyl Chloride) and Resistance to Adherence of Respiratory Bacterial Pathogens", Pharmaceutical Research 19(6): 818-824.
Journal of Ocular Pharmacology and Therapeutics, vol. 27, Issue 1, Table of Contents (Mary Ann Liebert, Inc. publishers), Retrieved from internet <URL:http://online.libertpub.com/toc/jop/27/1>, Downloaded Dec. 1, 2017, 5 pages.
K. Leszczynska et al., "Antibacterial activity of the human host defence peptide LL-37 and selected synthetic cationic lipids against bacteria associated with oral and upper respiratory tract infections", Journal of Antimicrobial Chemotherapy Advance Access, Published Nov. 7, 2012.
Louw et al., "Recueil des Travaux Chimiques des Pays-Bas et la Belgique", vol. 73, pp. 667 676, 1954.
Papo et al., "Host peptides as new weapons in cancer treatment", CMLS Cell. Mol. Life Sci. 62 (2005), 784-790.
Piktel et al. Sporicidal Activity of Ceragenin CSA-13 Against Bacillus Subtillis, Scientific Reports, vol. 7, Mar. 15, 2017 [retrieved on Apr. 24, 2018. Retreived from the internet: <URL: https://www.nature.com/articles/srep44452.pdf> Entire Document.
Polat et al., "In Vitro Amoebicidal Activity of a Ceragenin, Cationic Steroid Antibiotic-13, Against Acanthamoeba castellanii and Its Cytotoxic Potential", Journal of Ocular Pharmacology and Therapeutics, vol. 27, No. 1, 2011.
Press release (Ceragenix Pharmaceuticals, Wayne State University, Brigham Young University, Systemic Anti-Infectives, Preclinical Title—Ceragenin™ Compound demonstrates potent activity multidrug resistant bacterial strains of Pseudomonas, Denver, CO-Published Dec. 20, 2007).
Pycock, "The Dirty Mare", https://www.equine-reproduction.com/articles/DirtyMare.shtml, 2003.
Survey Research on Behcet's Disease, 2005 to 2007 Comprehensive Survey Reports, 2008, pp. 34-39.
Willemen et al., "Miceli Formation and Antimicrobial Acivity of Cholic Acid Derivatives with three Permanent Ionic Head Groups", Angew. Chem. Int. Ed., 2002, 41, No. 22.
Uncategorized: CSA Biotechnologies LLC, Apr. 5, 2011.
"Martindale: the complete drug reference, Cetrimide; Cetylpyridinium chloride ED-PARFITT K", Jan. 1, 2000, pp. 1105-1106.
Barton, Journal of Clinical Investigation, vol. 118, No. 2, Feb. 2008, Review Series, pp. 413-420.
Chen et al, J Drug Target, Dec. 2012; 20(10):856-63, 892.
Ogata et al. Intramammary application of ozone therapy to acute clinical mastitis in dairy cows. J. Vet. Med. Sci. 62(7): 681-686, 2000.
De Haas et al. Associations between pathogen-specific cases of clinical mastitis and somatic cell count patterns. J. Dairy Sci. 87: 95-105.
Weijian YE et al "Synthesis and antibacterial activity of new long-chain-alkyl bile acid-based amphiphiles", Bioorganic Chemistry, vol. 51, Aug. 19, 2013, pp. 1-7, XP55513451, US ISSN: 0045-2068, DOI:10.1013/j.bioorg.2013.08.003.
"Quaternary Ammoniuim Compounds", Van Nostrand's Scientific Encyclopedia, Jan. 1, 2006, John Wiley & Sons, Inc.
Opsenica D, et al., "Cholic Acid Derivatives as 1,2,4,5-Tetraoxane Carriers: Structure and Antimalarial and Antiproliferative Activity", J. Med Chem. Aug. 2000.
Valkonen, et al., "Bile acid amidoalcohols: simple organogelators", Biosens Bioelectron. 2004.
Deepak B. Salunke et al., "Amino Functionalized Novel Cholic Acid Derivatives Induce HIV-1 Replication and Syncytia Formation in T Cells", J. Med. Chem. 2006.
Ding, et al., "Correlation of the Antibacerial Activities of Cationic Peptid Antibiotics and Cationic Steroid Antibiotics", J. Med. Chem., vo. 45, pp. 663-669 (Year: 2002).
Kuroda, et al., "Ceragenin CSA-13 induces cell cycle arrest and antiproliferative effects in wild-type and p52 null mutant HCT116 colon cancer cells", Preclinical Report, Wolters Kluwer Health 2013.
U.S. Application Filed on Jul. 29, 2014, by Vazquez et al., U.S. Appl. No. 14/364,283.
U.S. Application Filed on Oct. 25, 2016, by Vazquez et al., U.S. Appl. No. 15/333,514.
U.S. Appl. No. 13/288,902, filed Nov. 3, 2011, Notice of Allowance dated Aug. 9, 2013.
U.S. Patent Application filed on Jul. 23, 2014 2014 by Vazquez et al., U.S. Appl. No. 14/339,342.
U.S. Patent Application Filed on Mar. 20, 2020, by Savage, U.S. Appl. No. 15/926,534.
Zaragoza Dorwald, Side Reactions in Organic Synthesis, 2005, Wiley-VCH Verlag GmbH & Co. KGaA, Weinheim, Preface, p. IX.

(56) References Cited

OTHER PUBLICATIONS

BASF, [Retrieved from internet <URL:https://worldaccount.basf.com/wa/NAFTA.about.en_US/Catalog/ChemicalsNAFTA-/doc4/BASF/PRD/30085231/.pdf?asset_type=pi/pdf&language=EN&urn=um:documen-tum: eCommerce_sol_EU:09007bb280022b53.pdf>] (Year: 2004).
csabiotech.com, Uncategorized: CSA Biotecfinologies LLC. posted by admin on Apr. 5, 2011 (Year: 2011).
Czemomysy-Furowicz et al. Etiological agents of mastitis in dairy cows on a farm in the West Pomeranian Region. Acta Sci. PoL, Zootechnica 7(1) 2008, 3-10.
Sigma-Aldrich, Poly(ethylene-co-vinyl acetate), [Retrieved from internet <URL:http://www.sigmaaldrich.com/catalog/product/aldrich/3405027lang—en (Registered) ion=US >], [Downloaded Jul. 22, 2016], excerpt in action.
"mouth rinse" definition by Medical dictionay Retrieved from http://medical-dictionary.thefreedictionary.com/mouth-i-rinse.
Ahmed, Hydrogel: Preparation, characterization, and applications: A review, Journal of Advanced Research (2015) 6: 105-121 (Year: 2015).
BASF, [Retrieved from internet <URL: https://worldaccount.basf.com/wa/NAFTA.about.en_US/Catalog/ChemicalsNAFTA-/doc4/BASF/PRD/30085231/.pdf?asset_type=pi/pdf&language=EN&urn=um:documen-tum:eCommerce_sol_EU:09007bb280022b53.pdf >] (Year: 2004).
Bondaryk et al. Postep. Derm. Alergol., 2013, vol. 5, pp. 293-301.
csabiotech.com. Uncategorized: CSA Biotechnologies LLC. posted by admin on Apr. 5, 2011 (Year: 2011).
Czernomysy-Furowicz et al. Etiological agents of mastitis in dairy cows on a farm in the West Pomeranian Region. Acta Sci Pol., Zootechnica 7(1) 2008, 3-10.
Dean et al.; Flavor Associated with Fish Meal in Diets Fed to Broiler Chickens; 1968; Can. J. Animal Sci.; 49:11-15 (Year: 1968).
Dumortier, Getal. (Pharmaceutical Research, vol. 23, No. 12, Dec. 2006).
FENG, Theses Brigham Young University, BYU Scholars Archive, dated Dec. 19, 2011, 892.
Ganot (WO 2009/144708 A) (Year: 2009).
International Search Report for PCT Application No. PCT/US2009/0475485 dated Feb. 17, 2010.
Jacob; Feeding Fishmeal to Poultry; https://articles.extension.org/pages/67357/feeding-fishmeal-to-poultry; May 5, 2015; accessed Sep. 10, 2018 (Year: 2015).
K. Leszczynska et al., "Potential of ceragin CSA-13 and its mixture with pluronic F-127 as treatment of topical bacterial infections", Journal of Applied Microbiology, vol. 110, No. 1, Oct. 21, 2010, pp. 229-238.
Kaltsas et al., Endocrine-Related Cancer (2005) 12 683-699.
Leszczynska et al. (J Antimicrob Chemother, published Nov. 7, 2012), Bacterial activity of cationic lipids, pp. 1-9).
No author listed. Novel antibiotic coating shows potential for use on surgical implants. Healio website. Dec. 21, 2005. healio.com/orthopedics/news/online/%7BdcOe6031-1f10-4b3c-abf6-f50b9cfd683f%7D/novel-antibiotic-coating-shows-potential-for-use-on-surgical-implants. Accessed Jun. 2, 2019. (Year: 2005).
Notice of Allowance received for U.S. Appl. No. 14/257,776, dated Mar. 25, 2016.
Office Action received for U.S. Appl. No. 14/257,776, dated Apr. 16, 2015.
Oxford Dictionaries (on-line) definition of Adsorb ([Retrieved from internet <URL: http://www.oxforddictionaries.com/us/definition/american_english/adsorb >] [Downloaded Mar. 10, 2015]).
Pollard et al. (J Antimicrob Chemother 2012; 67:2665-2672).
Rausch, Virtual Textbook of Organic Chemistry, Heterocyclic Chemistry, 1999, pp. 1-14, recovered from https://www2.chemistry.msu.edu/faculty/reusch /VirtTxtJml/heterocy.htm on Jun. 1, 2017.
Sigma-Aldrich, Poly(ethylene-co-vinyl acetate), [Retrieved from internet <URL: http://www.sigmaaldrich.com/catalog/product/aldrich/3405027lang= en®ion=US >], [Downloaded Jul. 22, 2016], excerpt in action.
Staphylococcal Infections (Electronic Resource; Merck Manual). Retrieved on Jul. 3, 2017: [http://www.merckmanuals.com/professional/infectious-diseases/gram-positive-cocci/staphylococcal-infections].
U.S. Appl. filed Apr. 22, 2016, Savage et al., U.S. Appl. No. 15/135,928.
U.S. Appl. filed Apr. 23, 2015, Beus et al., 14694028.
U.S. Appl. filed Apr. 7, 2017, Savage., U.S. Appl. No. 15/481,184.
U.S. Appl. filed Apr. 7, 2017, Savage., U.S. Appl. No. 15/481,884.
U.S. Appl. filed Aug. 19, 2015, Savage., U.S. Appl. No. 14/830,356.
U.S. Appl. filed Jan. 16, 2017, Savage., U.S. Appl. No. 15/406,667.
U.S. Appl. filed Jan. 21, 2015, Savage., U.S. Appl. No. 14/602,071.
U.S. Appl. filed Jan. 22, 2015, Savage., U.S. Appl. No. 14/602,499.
U.S. Appl. filed Jul. 25, 2014, Savage, et al., U.S. Appl. No. 14/341,304.
U.S. Appl. filed Jun. 25, 2015, Genberg et al., U.S. Appl. No. 14/750,928.
U.S. Appl. filed Mar. 11, 2015, Beus et al., U.S. Appl. No. 14/644,946.
U.S. Appl. filed Mar. 11, 2015, Savage et al., U.S. Appl. No. 14/645,040.
U.S. Appl. filed Mar. 23, 2018, Savage, Paul B., U.S. Appl. No. 15/934,534.
U.S. Appl. filed Mar. 9, 2017, Savage et al., U.S. Appl. No. 15/454,135.
U.S. Appl. filed May 3, 2017, Savage et al., U.S. Appl. No. 15/585,632.
U.S. Appl. filed Oct. 16, 2014, Savage, et al., U.S. Appl. No. 14/515,858.
U.S. Appl. filed Oct. 30, 2014, Savage, et al., U.S. Appl. No. 14/398,094.
U.S. Appl. filed Oct. 6, 2015, Savage., U.S. Appl. No. 14/875,953.
U.S. Appl. filed Sep. 1, 2015, Genberg et al., U.S. Appl. No. 14/842,582.
U.S. Appl. filed Sep. 20, 2016, Genberg et al., U.S. Appl. No. 15/270,876.
U.S. Appl. filed Sep. 9, 2015, Genberg et al., U.S. Appl. No. 14/848,819.
U.S. Appl. No. 13/841,549, filed Mar. 15, 2013, Office Action dated Apr. 23, 2015.
U.S. Appl. No. 14/288,126, filed May 27, 2014, Savage et al.
U.S. Appl. No. 14/341,304, filed Feb. 21, 2017, Final Office Action dated Feb. 21, 2017.
U.S. Appl. No. 14/926,738, filed Oct. 29, 2015, Vazquez et al.
U.S. Application filed Feb. 17, 2015, by Savage, U.S. Appl. No. 14/624,200.
U.S. Application filed Mar. 10, 2015, by Darien et al., U.S. Appl. No. 14/642,905.
Final Office Action received for U.S. Appl. No. 14/750,928, dated Feb. 7, 2019, 28 pages.
Non-Final Office Action received for U.S. Appl. No. 14/750,928, dated Jan. 11, 2017, 13 pages.
Non-Final Office Action received for U.S. Appl. No. 14/750,928, dated Jul. 7, 2017, 18 pages.
Examiner Interview Summary received for U.S. Appl. No. 14/208,082, dated Oct. 23, 2020, 4 pages.
Final Office Action received for U.S. Appl. No. 14/208,082, dated Oct. 16, 2020, 17 pages.
Final Office Action received for U.S. Appl. No. 14/341,304, dated Oct. 16, 2020, 18 pages.
Final Office Action received for U.S. Appl. No. 14/515,858, dated Oct. 23, 2020, 26 pages.
Final Office Action received for U.S. Appl. No. 15/926,534, dated Oct. 21, 2020, 8 pages.
Final Office Action received for U.S. Appl. No. 15/135,928, dated Jun. 5, 2020, 11 pages.
Non-Final Office Action received for U.S. Appl. No. 15/926,577, dated Sep. 28, 2020, 14 pages.
Dennison et al., "Anticancer a-Helical Peptides and Structure/Function Relationships Underpinning their Interactions with Tumour Cell Membranes", Current Protein and Peptide Science, 2006, 7, No. 6, pp. 1-13.

(56) References Cited

OTHER PUBLICATIONS

Ding, et al., "Origins of cell selectivity of cationic steroid antibiotics", Journal of American Chemical Society, Oct. 2004, pp. 13642-13648.

International Search Report and Written Opinion received for PCT Patent Application No. PCT/US2020/034297, dated Aug. 26, 2020, 8 pages.

Papo et al., "Host defense peptides as new weapons in cancer treatment", Cmls Cellular and Molecular Life Sciences, vol. 62, No. 7-8, Apr. 1, 2005, pp. 784-790.

* cited by examiner

CSA-37

CSA-41

CSA-42

CSA-43

CSA-44

CSA-45

CSA-47

CSA-49

CSA-50

CSA-51

CSA-1

CSA-2

CSA-3

CSA-4

CSA-5

CSA-6

CSA-7

CSA-8

CSA-10

CSA-11

CSA-22

CSA-23

CSA-24

CSA-25

CSA-26

CSA-38

CSA-39

CSA-40

CSA-46

CSA-48

CSA-53

CSA-54

CSA-55

CSA-57

CSA-58

CSA-59

CSA-60

CSA-90

CSA-91

CSA-92

CSA-92 FL

CSA-93

CSA-94

CSA-95

CSA-96

CSA-105

CSA-106

CSA-107

CSA-109

CSA-110

CSA-112

CSA-113

CSA-118

CSA-119

CSA-120

CSA-121

CSA-121a

CSA-122

CSA-123

CSA-124

CSA-130

CSA-131

CSA-132

CATIONIC STEROIDAL ANTIBIOTIC COMPOSITIONS FOR THE TREATMENT OF DERMAL TISSUE

CROSS-REFERENCE TO RELATED APPLICATIONS

This application is a continuation of U.S. patent application Ser. No. 15/454,135, filed Mar. 9, 2017, which claims the benefit of U.S. Provisional Patent Application Ser. No. 62/306,810, filed Mar. 11, 2016, and U.S. Provisional Patent Application Ser. No. 62/412,079, filed Oct. 24, 2016, the disclosures of which are incorporated herein by reference in their entirety.

BACKGROUND

1. Field of Disclosure

The disclosure relates generally to treatment compositions for the treatment of dermal tissue, including treatment compositions useful as soft tissue fillers and/or tissue glues, which incorporate one or more cationic steroidal antimicrobial (CSA) compounds to provide one or more of antimicrobial activity, anti-inflammatory activity, reduced pain, and increased rate of tissue healing.

2. Related Technology

Many treatment compositions are introduced into or applied onto a subject's tissues. For example, soft tissue fillers (also commonly referred to as dermal fillers or injectable implants) are often injected into the dermal layers of the face to create a smoother or fuller appearance, or are injected in other dermal areas for cosmetic or medical reasons. Some medical compounds are used as tissue glues for the fixation and closure of tissue openings, wounds, and lacerations. Tissue glues are commonly formed from a cyanoacrylate compound. In some instances, tissue glues can negate or reduce the amount of suturing/stitching required to close a tissue wound. Some tissue glues are also used to occlude fistulas or to embolize blood vessels.

These treatment compositions can be used to provide several medical benefits. However, even when strict sterilization procedures are followed, such treatment compositions can be subject to microbial contamination, including biofilm formation. In addition, the related procedures can inadvertently introduce microbes into the associated tissues, even if the treatment compositions and targeted tissues were initially sterile. When biofouling of the composition occurs, infection and subsequent medical complications can occur. Typically, the resulting composition (e.g., the injected dermal filler or the hardened tissue glue) must be removed from the subject, the subject must be retreated to correct the deficiency caused by the removal, and the subject must be treated with antibiotics to address the infection and/or to prevent reinfection.

In some cases, biofouling can be associated with even more detrimental health effects. In many circumstances, the applied and/or injected treatment composition serves as a site for microbial contamination and biofilm formation, which can lead to recurrent and difficult to manage infections. These infections can occur at tissue near the treatment site, or can even spread and occur at other remote locations in a subject's body. A microbial infection associated with a fouled composition can cause serious health problems for the patient, and can even lead to very serious and deadly conditions, such as sepsis. Even when treatable, these types of infections require additional medical care, with its concomitant costs, prolonged healing times, and patient discomfort.

In addition, the injection and/or application of a treatment composition can trigger an inflammatory response from the subject, even in the absence of any corresponding infection. This can occur because of the subject's reaction to the introduction of an unknown and foreign substance. In many instances, even if the composition itself is bio-inert, the way by which it is deployed requires the composition to be contacted against surrounding tissues, which can aggravate the surrounding tissues and lead to inflammation and pain.

BRIEF SUMMARY

Embodiments disclosed herein are directed to treatment compositions for the treatment of dermal tissues. The compositions incorporate one or more CSA compounds to provide effective antimicrobial properties and/or anti-inflammatory properties. In some embodiments, the treatment compositions incorporating one or more CSA compounds are additionally or alternatively provided with effective analgesic properties and/or tissue healing properties. In at least some embodiments, a treatment composition incorporating one or more CSA compounds is capable of exhibiting anti-inflammatory and/or wound healing properties independent of any antimicrobial properties.

Non-limiting examples of dermal treatment compositions that incorporate one or more CSA compounds, as described herein, include soft tissue fillers, tissue glues, and injectable or other subcutaneous dermatological compositions. For example, some embodiments a composition incorporating one or more CSA compounds is configured as a soft tissue filler, such as a soft tissue filler including collagen, hyaluronic acid, hydroxyapatite minerals (e.g., calcium hydroxyapatite), poly-l-lactic acid (PLLA), other bioabsorbable filler materials, non-absorbable biocompatible materials (e.g., silicone or polymethylmethacrylate materials), or combinations thereof. In other embodiments, tissue glue compositions incorporating one or more CSA compounds include one or more cyanoacrylate compounds configured for use in closing wounds (e.g., lacerations, surgical incisions, cuts, etc.), embolizing blood vessels, and/or occluding fistulas. In still other embodiments, an injectable treatment composition includes a CSA compound and one other active compound, such as botox.

In preferred embodiments, the one or more CSA compounds are provided in salt form, such as a naphthalenedisulfonic acid (NDSA) salt, including 1,5-NDSA salt. The NDSA salt of CSA-131 is an example of an effective compound for use in making the treatment compositions disclosed herein, including tissue glues, dermal fillers, injectable or subcutaneous compositions, and the like.

In some embodiments, a composition for dermal treatment which includes one or more CSA compounds provides antimicrobial properties, and thereby provides the benefits of reducing fouling of the injected and/or applied material, reducing infection risk associated with fouling of the material, reducing infection-related inflammation associated with the treatment, reducing patient discomfort associated with an infection, and/or enabling more positive outcomes following a medical treatment involving such a treatment composition.

In some embodiments, a treatment composition including one or more CSA compounds provides the benefits of reducing pain, swelling and inflammation and/or increasing the rate of tissue healing even in the absence of any microbial contamination or infection. Thus, at least some of the treatment compositions described herein provide, independently, the benefits of anti-microbial functionality, anti-inflammatory functionality, analgesic functionality, anti-swelling functionality, and tissue healing functionality.

While the embodiments described herein are not limited to any particular mechanism, it is believed that in at least some applications an increased rate of tissue healing is caused by increases in fibroblastic migration and enhanced epithelial growth factors at the treatment site. Subjects have also exhibited a significantly sensitivity to pain. In some embodiments, the therapeutic anti-inflammatory effect is derived from the steroid-like structure of the CSA compounds and/or effects in modulating genes related to inflammation, and the anti-inflammatory effect is independent of any anti-microbial activity. However, anti-inflammatory activity may be exhibited because of anti-microbial effects of the CSA compounds as well. Anti-pain properties are associated with modulation of $P2X_7$ receptors.

One or more embodiments are directed to methods of controlling microbial growth on injected and/or applied composition material and/or at a treatment site at which a treatment composition is applied, and likewise controlling the spread of microbial growth to other areas of a subject's body (e.g., to prevent a septic infection). For example, one or more embodiments are directed to controlling biofilm formation on injected/applied material. In some embodiments, a method includes (1) injecting and/or applying a treatment composition having one or more incorporated CSA compounds at a dermal tissue site, and (2) the treatment composition killing one or more microbes contacting the treatment composition. The composition may be effective in killing a wide variety of microbes (e.g., a wide variety of different bacterial strains).

One or more embodiments are directed to methods of reducing inflammation at a treatment site at which a treatment composition is injected and/or applied. In some embodiments, a method includes (1) injecting and/or applying a treatment composition containing one or more CSA compounds at a dermal tissue site, and (2) the treatment composition reducing or preventing inflammation at the treatment site (e.g., as compared to a similar treatment composition not incorporating CSA compounds).

Certain embodiments are directed to methods of increasing the rate of tissue healing at a treatment site at which a treatment composition has been injected and/or applied. In some embodiments, a method includes (1) injecting and/or applying a treatment composition having one or more incorporated CSA compounds at a dermal tissue site, and (2) the treatment composition increasing the rate of tissue healing at the treatment site (e.g., as compared to a similar treatment composition not incorporating CSA compounds).

In some embodiments, a method of manufacturing a treatment composition with one or more incorporated CSA compounds includes: (1) providing a biologically compatible material suitable for application onto or injection into dermal tissue; and (2) mixing one or more CSA compounds with the biologically compatible material.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

BRIEF DESCRIPTION OF DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION

I. Overview of CSA Compounds

Cationic sterioidal antibiotic ("CSA") compounds ("CSAs"), also known as "ceragenin" compounds (or "ceragenins"), are synthetically produced small molecule chemical compounds that include a sterol backbone having various charged groups (e.g., amine, guanidine, and/or other groups capable of exhibiting cationic properties under biological conditions) attached to the backbone. The backbone can orient the cationic groups on one face, or plane, of the sterol backbone.

CSA compounds are cationic and amphiphilic based upon the functional groups attached to the backbone. They are facially amphiphilic with a hydrophobic face and a polycationic face. Without wishing to be bound to any particular theory, it is theorized that the CSA compounds described herein act as anti-microbial agents (e.g., anti-bacterials, anti-fungals, and anti-virals) by binding to the cellular membrane of bacteria and other microbes and inserting into the cell membrane, forming a pore that allows the leakage of ions and cytoplasmic materials that are critical to the microbe's survival, thereby leading to the death of the affected microbe. In addition, the CSA compounds described herein may also act to sensitize bacteria to antibiotics. For example, at concentrations of the CSA compounds below the corresponding minimum bacteriostatic concentration, CSA compounds have been shown to cause bacteria to become more susceptible to other antibiotics by increasing the permeability of the membrane of the bacteria.

The charged groups are responsible for disrupting the bacterial cellular membrane; without the charged groups, the CSA compound cannot disrupt the membrane to cause cell death or sensitization. Example CSA compounds shown below can have the structure of Formula I. As will be discussed in greater detail below, the R groups of Formula I can have a variety of different functionalities, thus providing a given ceragenin compound with specific, different properties. In addition, as will be appreciated by those of skill in the art, the sterol backbone can be formed of 5-member and/or 6-member rings, so that p, q, m, and n may independently be 1 (providing a 6-member ring) or 0 (providing a 5-member ring).

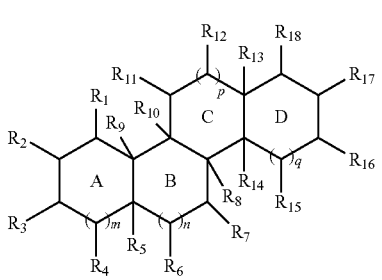

(I)

Figure 1A:
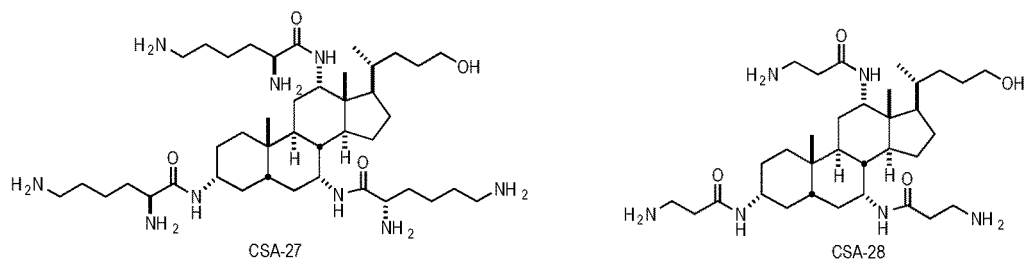
FIG. 1A illustrates examples of cationic steroidal antimicrobial compounds having ester and amide linkages at one or more of the $R_3$, $R_7$, and $R_{12}$ positions.
Figure 1A:
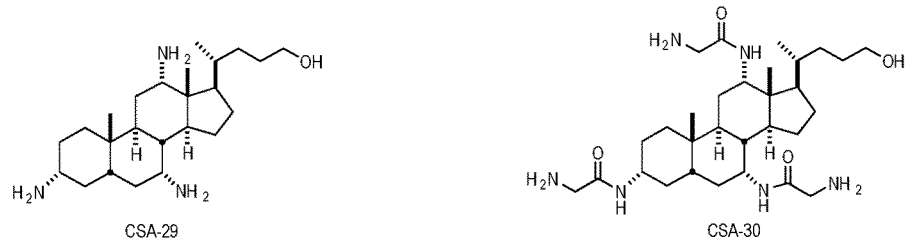
Figure 1A:
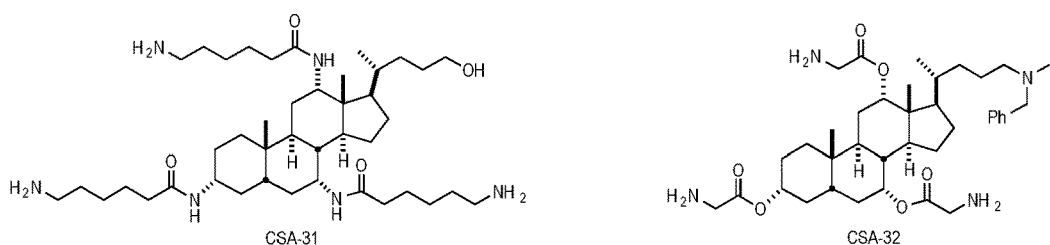
Figure 1A:
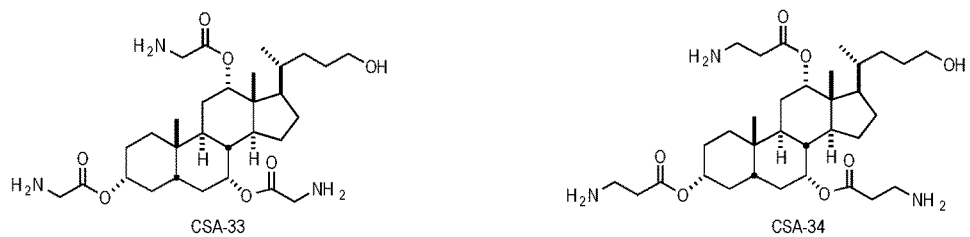
Figure 1A:
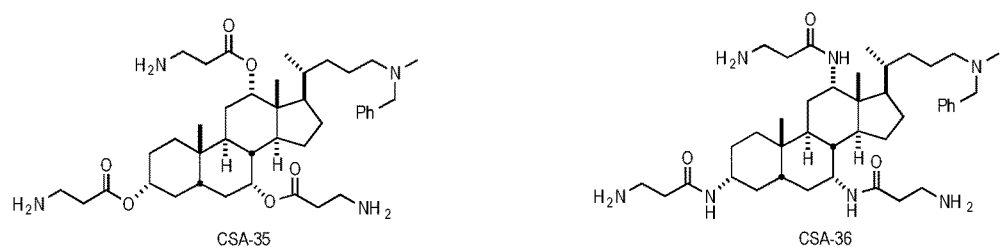
Figure 1A:
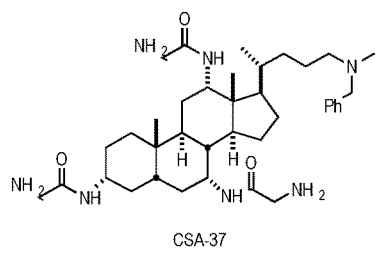
Figure 1A:
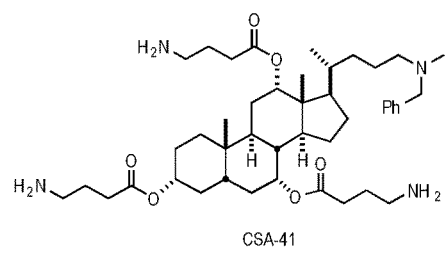
Figure 1A:
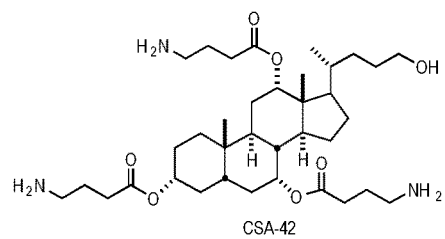
Figure 1A:
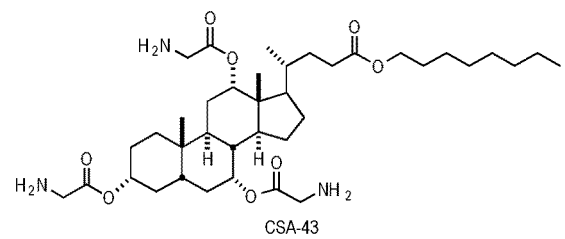
Figure 1A:
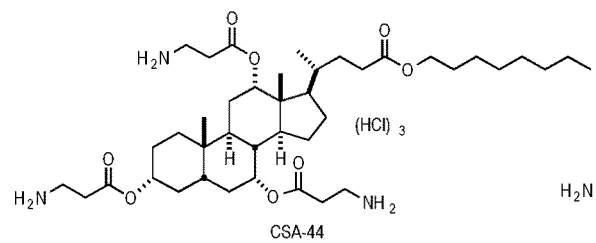
Figure 1A:
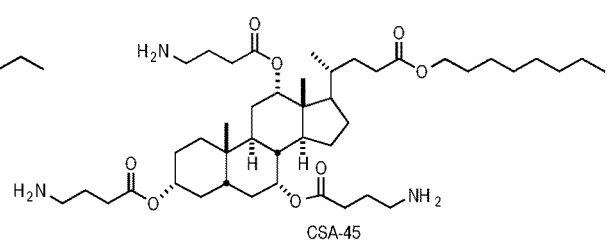
Figure 1A:
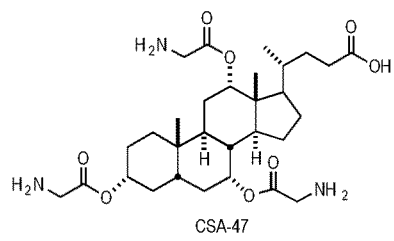
Figure 1A:
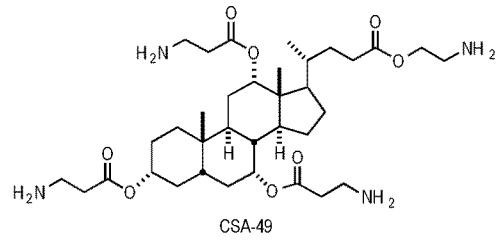
Figure 1A:
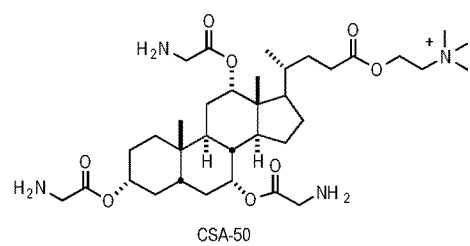
Figure 1A:
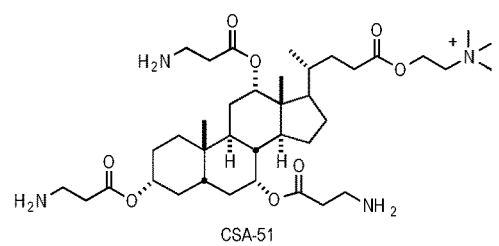
Figure 1A:
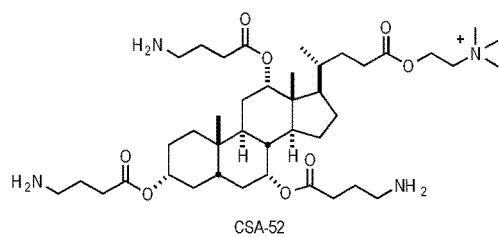
Figure 1A:
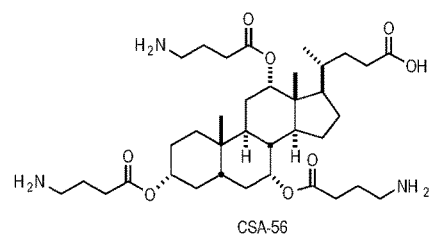
Figure 1A:
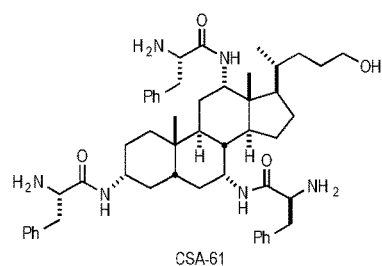
Figure 1A:
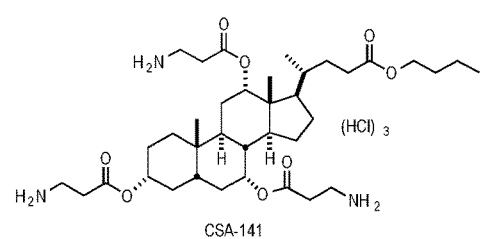
Figure 1A:
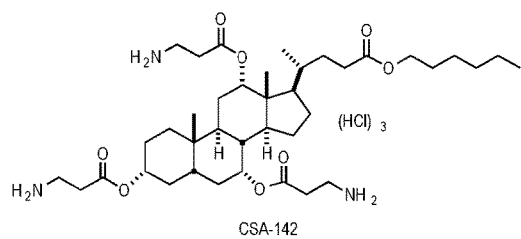
Figure 1A:
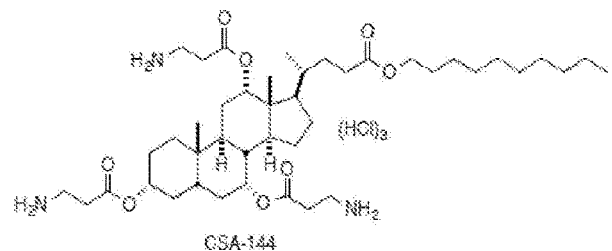
Figure 1A:
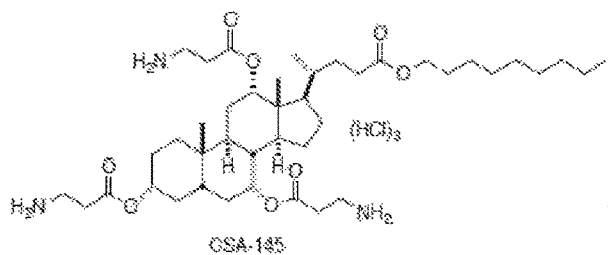
Figure 1A:
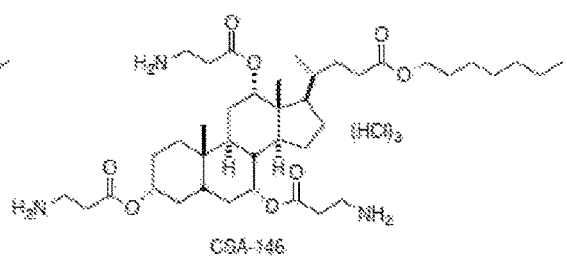
Figure 1B:
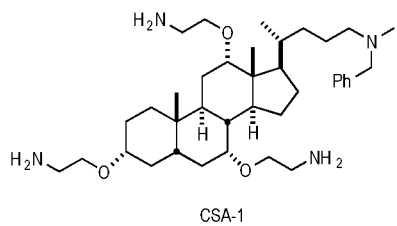
FIG. 1B illustrates examples of cationic steroidal antimicrobial compounds having ether linkages at one or more of the $R_3$, $R_7$, and $R_{12}$ positions.
Figure 1B:
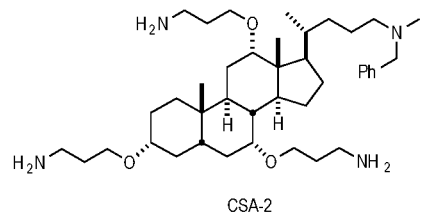
Figure 1B:
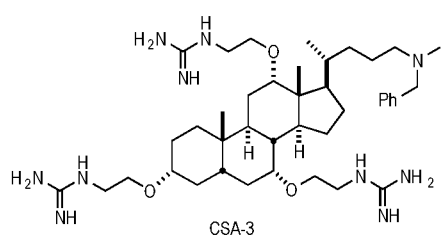
Figure 1B:
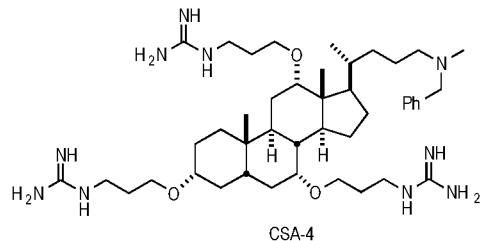
Figure 1B:
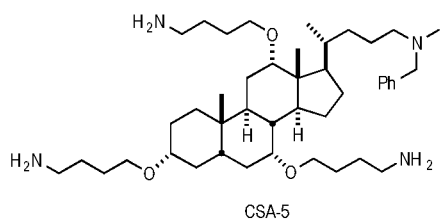
Figure 1B:
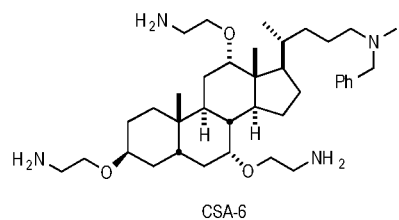
Figure 1B:
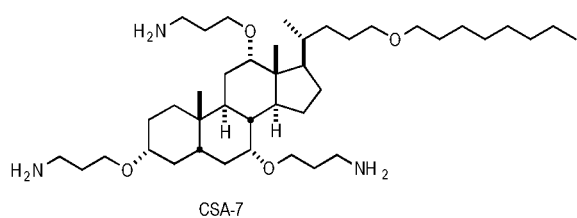
Figure 1B:
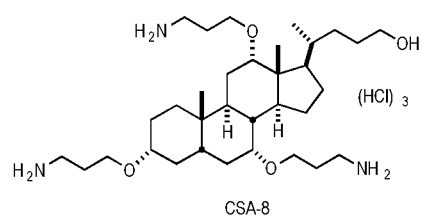
Figure 1B:
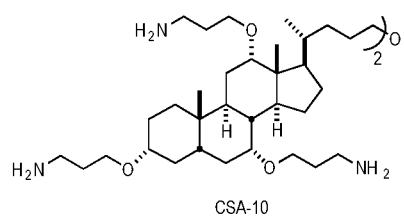
Figure 1B:
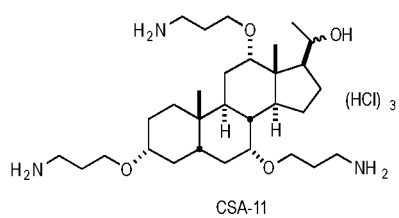
Figure 1B:
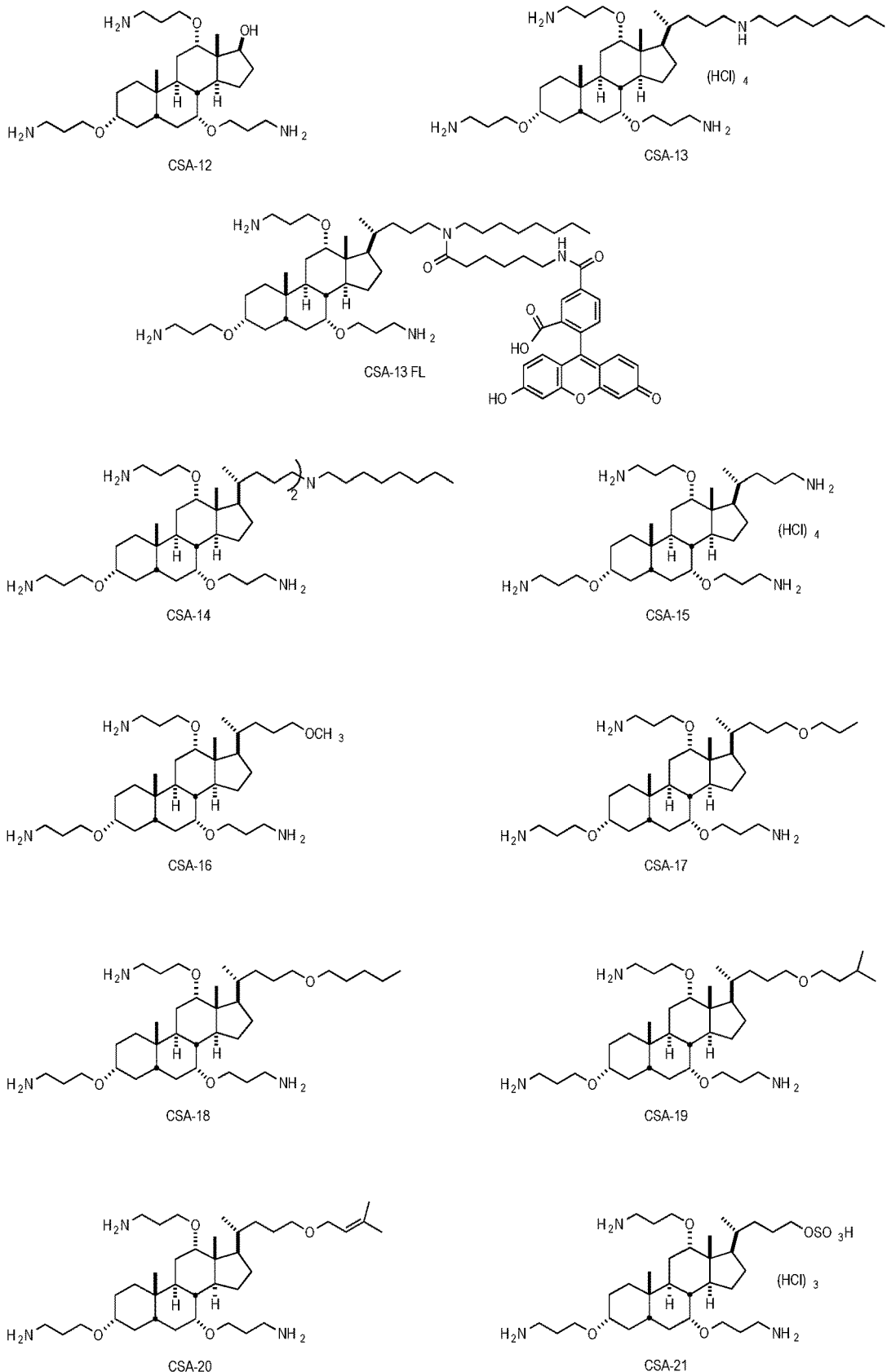
Figure 1B:
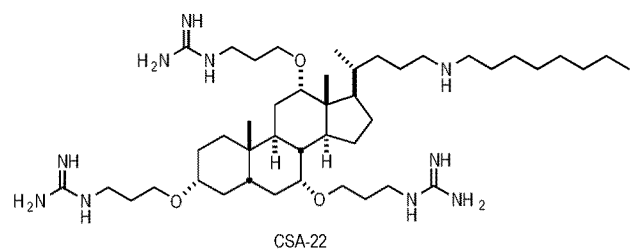
Figure 1B:
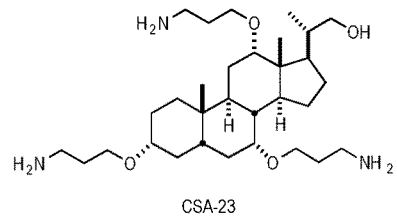
Figure 1B:
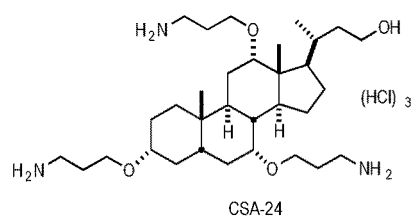
Figure 1B:
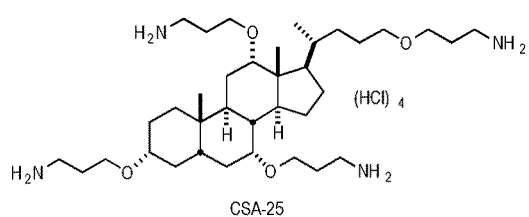
Figure 1B:
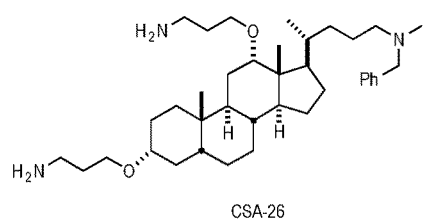
Figure 1B:
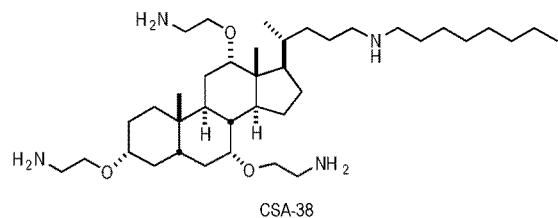
Figure 1B:
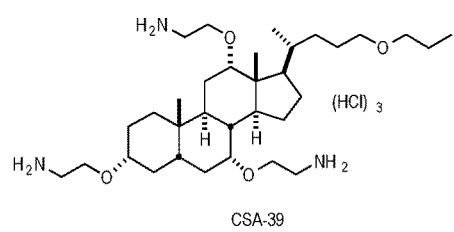
Figure 1B:
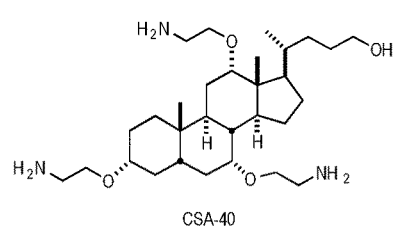
Figure 1B:
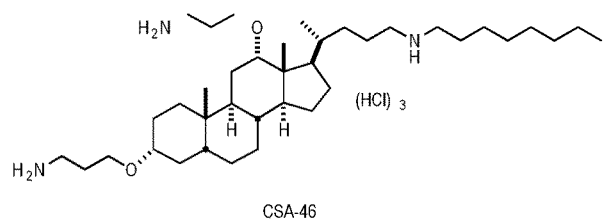
Figure 1B:
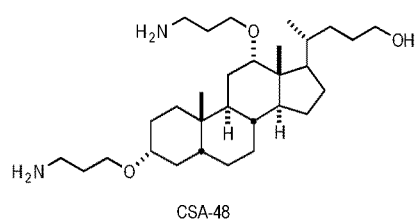
Figure 1B:
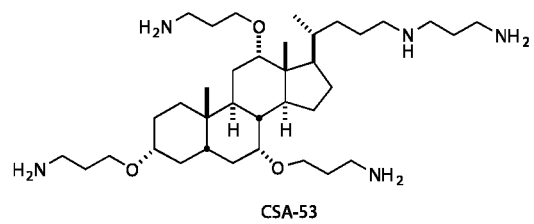
Figure 1B:
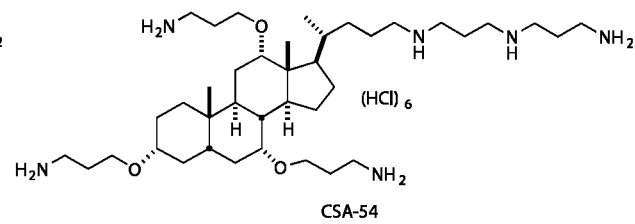
Figure 1B:
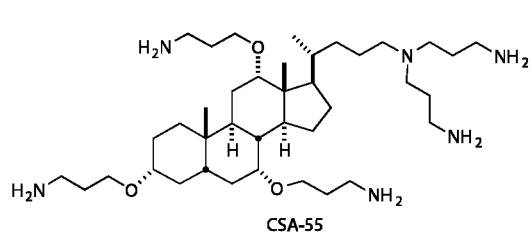
Figure 1B:
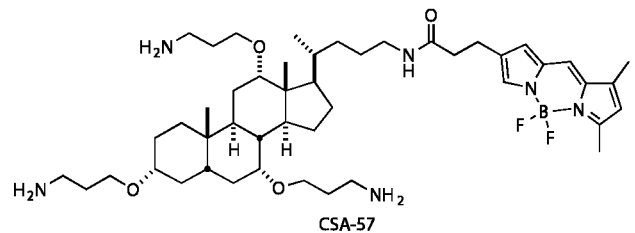
Figure 1B:
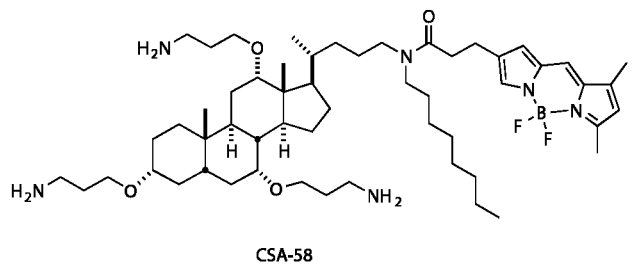
Figure 1B:
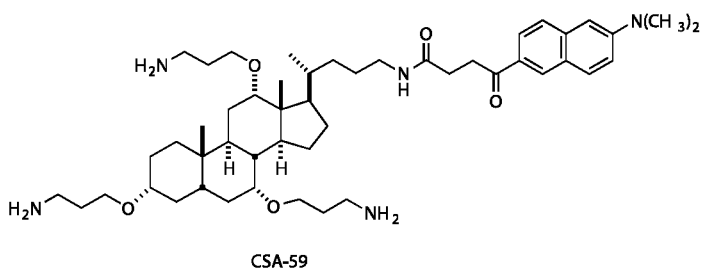
Figure 1B:
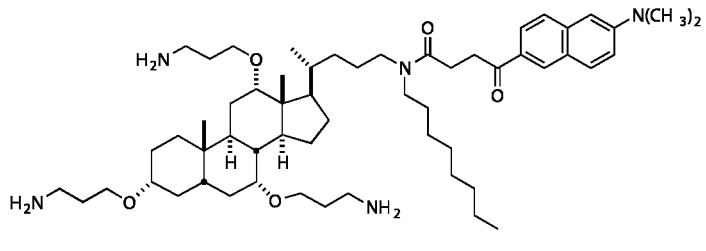
Figure 1B:
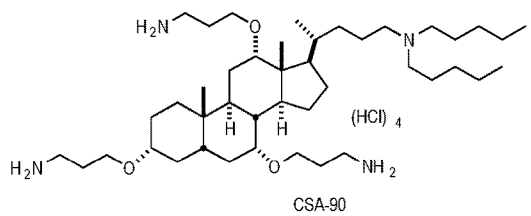
Figure 1B:
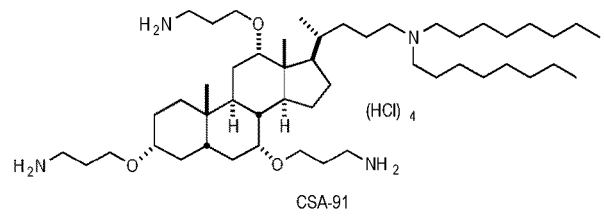
Figure 1B:
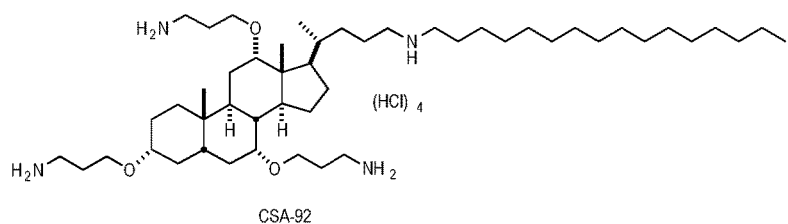
Figure 1B:
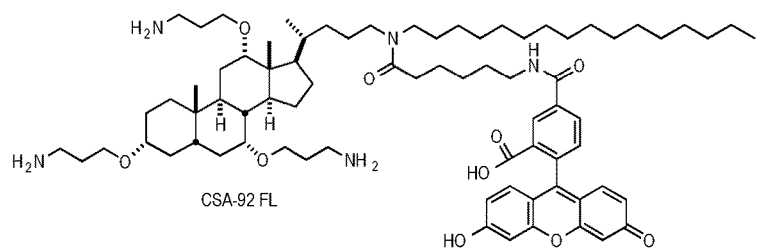
Figure 1B:
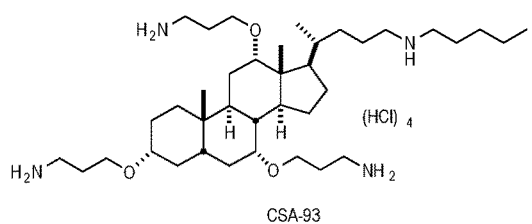
Figure 1B:
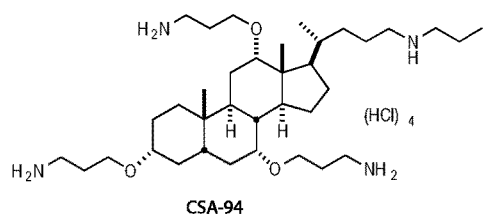
Figure 1B:
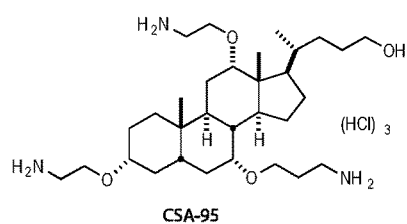
Figure 1B:
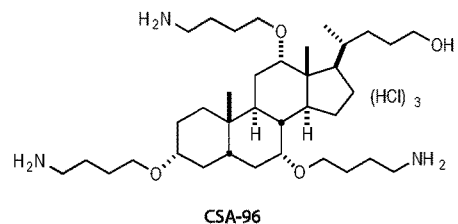
Figure 1B:
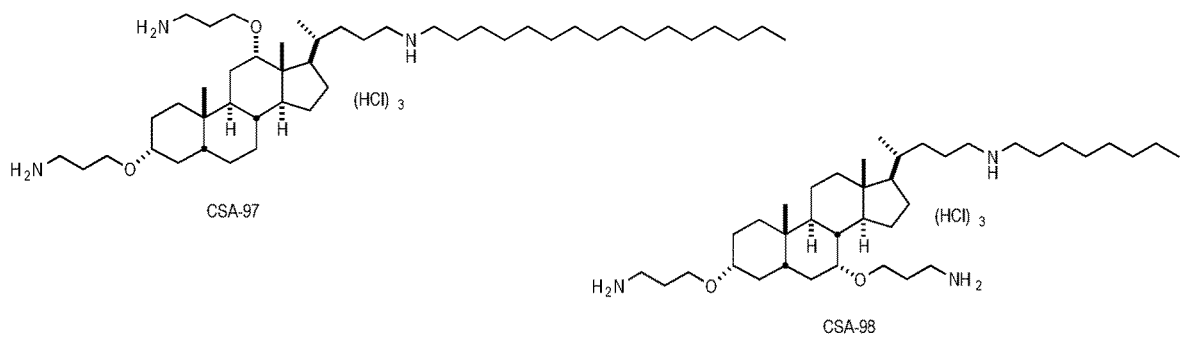
Figure 1B:
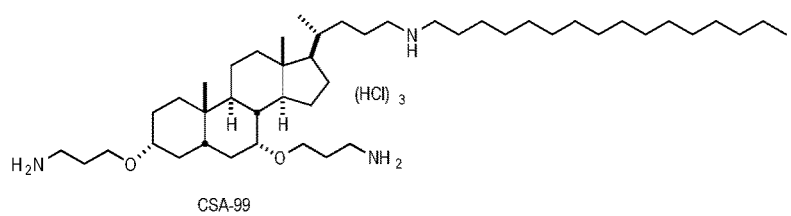
Figure 1B:
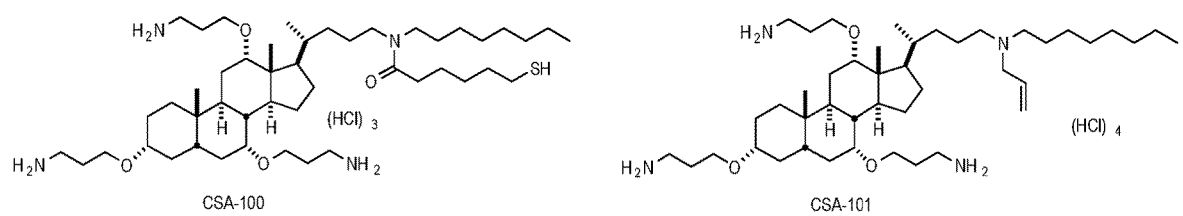
Figure 1B:
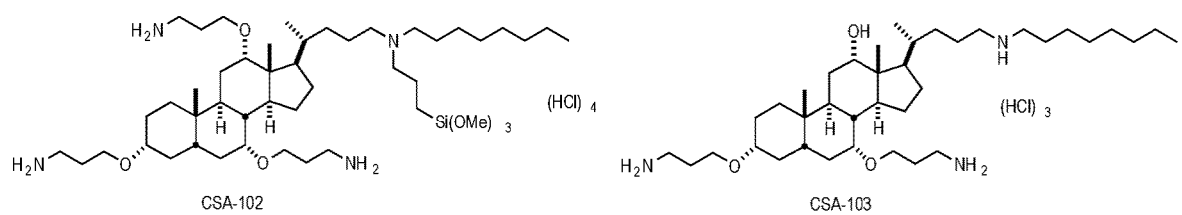
Figure 1B:
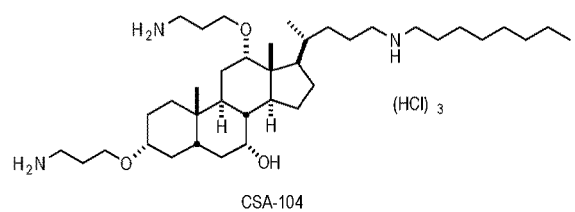
Figure 1B:
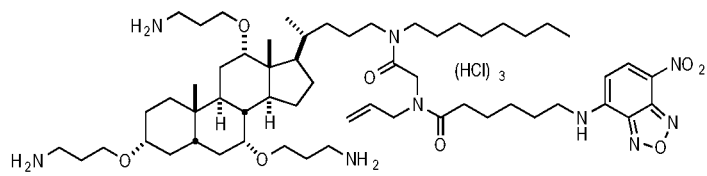
Figure 1B:
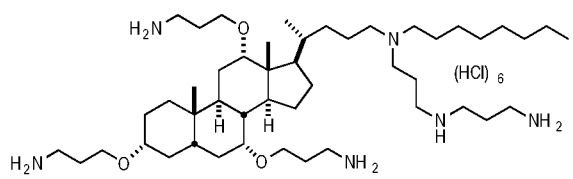
Figure 1B:
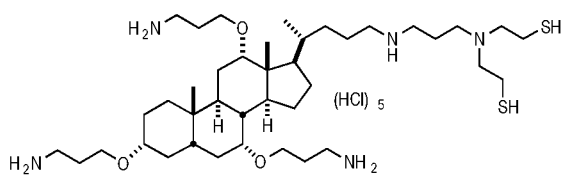
Figure 1B:
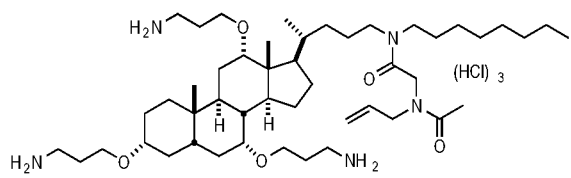
Figure 1B:
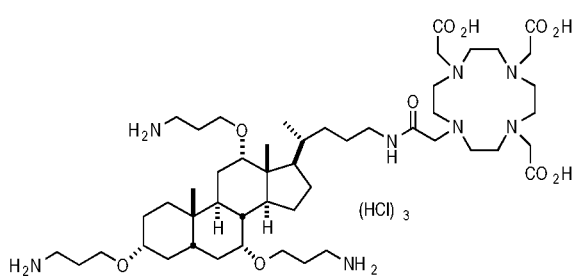
Figure 1B:
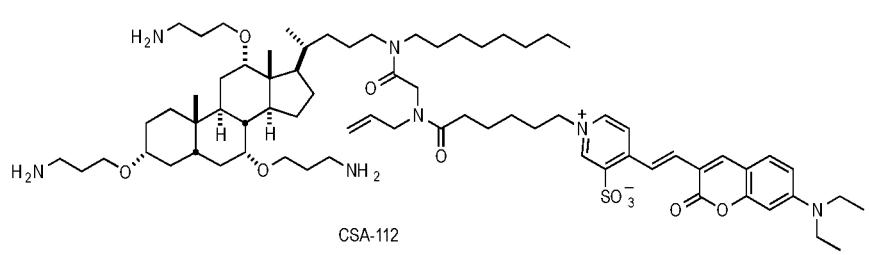
Figure 1B:
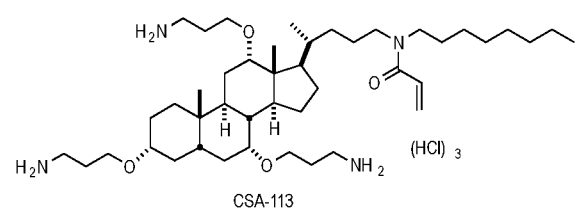
Figure 1B:
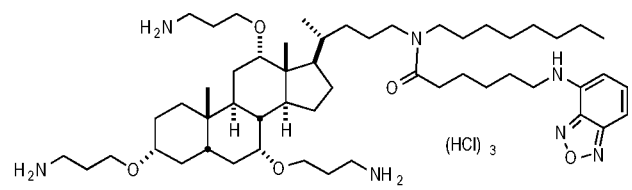
Figure 1B:
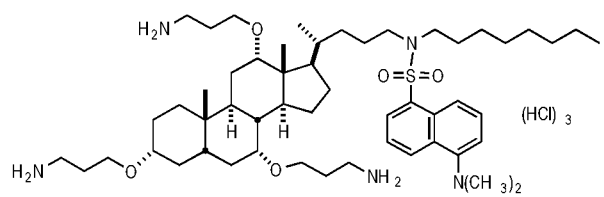
Figure 1B:
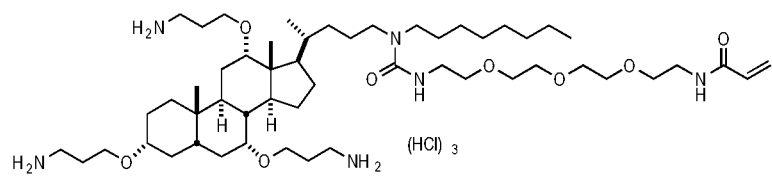
Figure 1B:
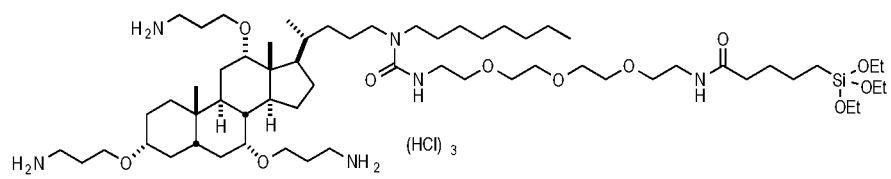
Figure 1B:
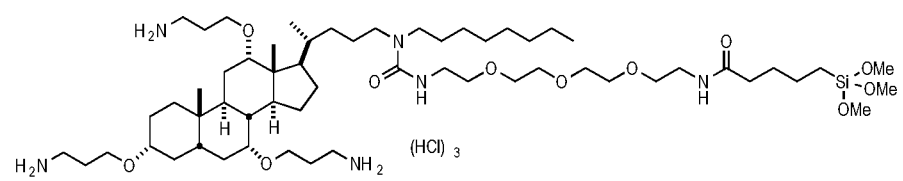
Figure 1B:
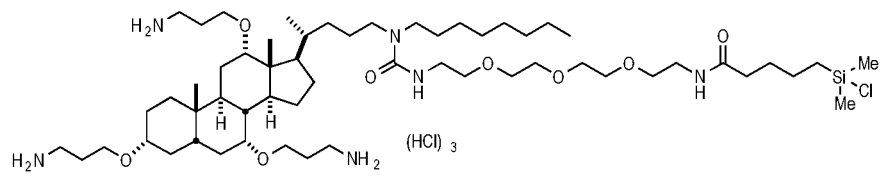
Figure 1B:
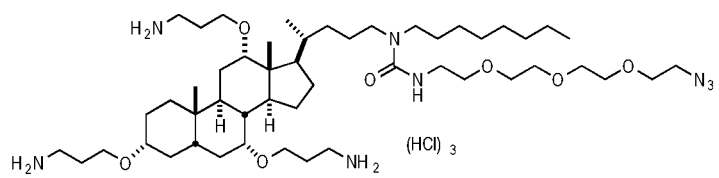
Figure 1B:
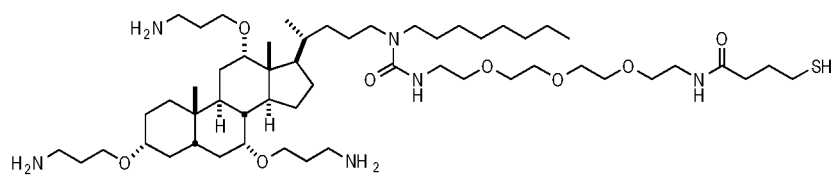
Figure 1B:
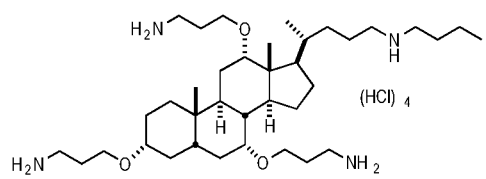
Figure 1B:
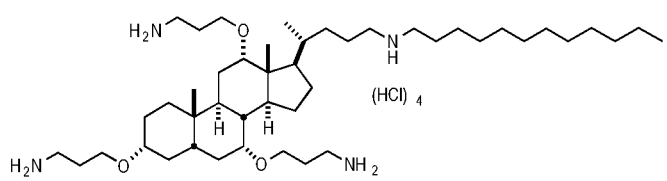
Figure 1B:
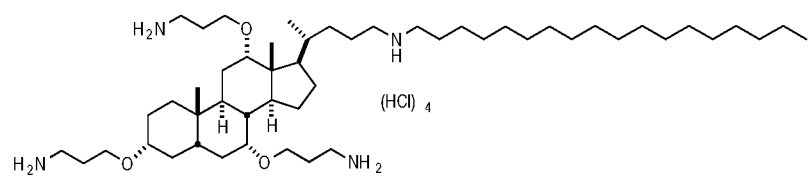
Figure 1B:
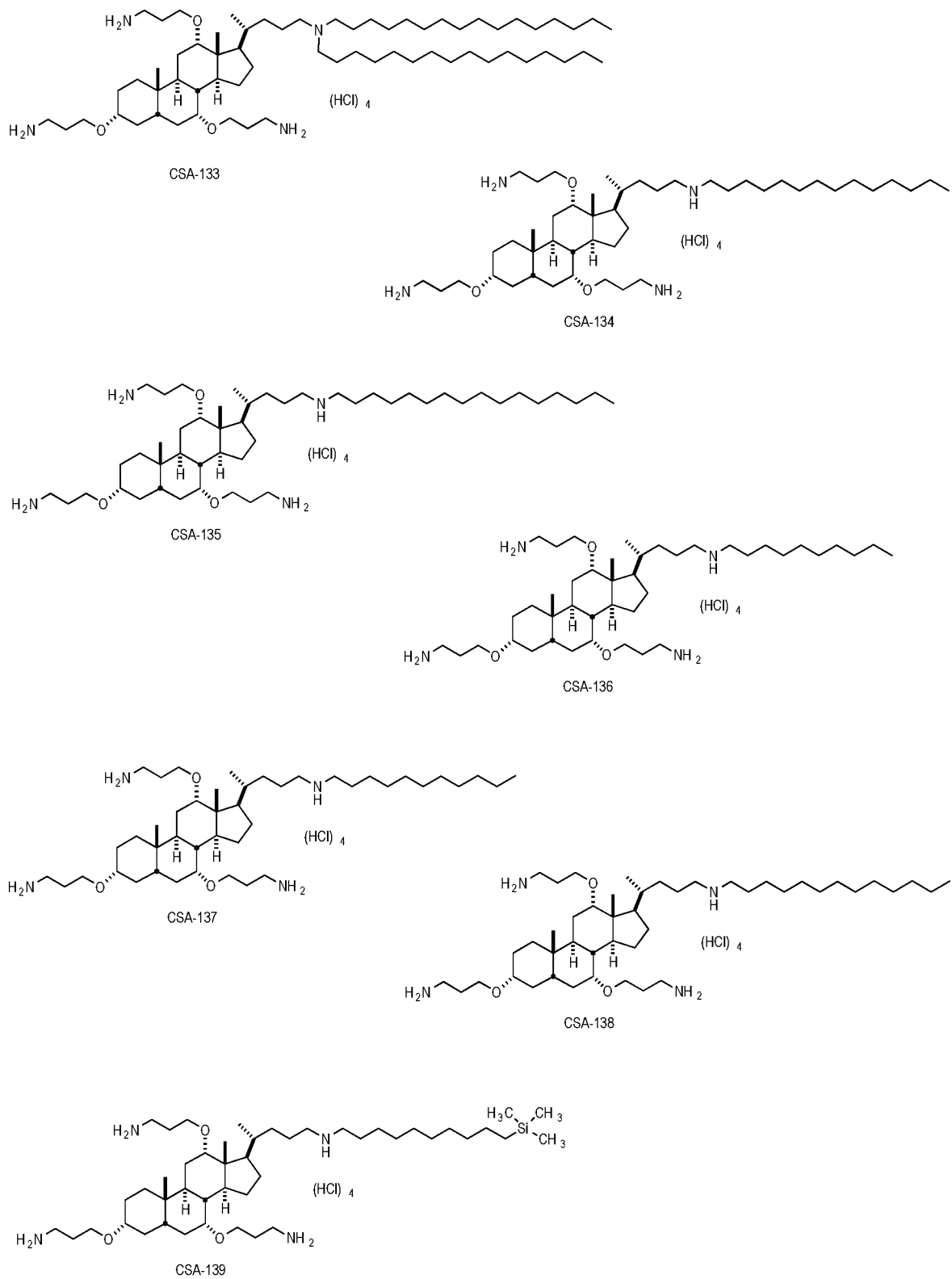
Figure 1C:
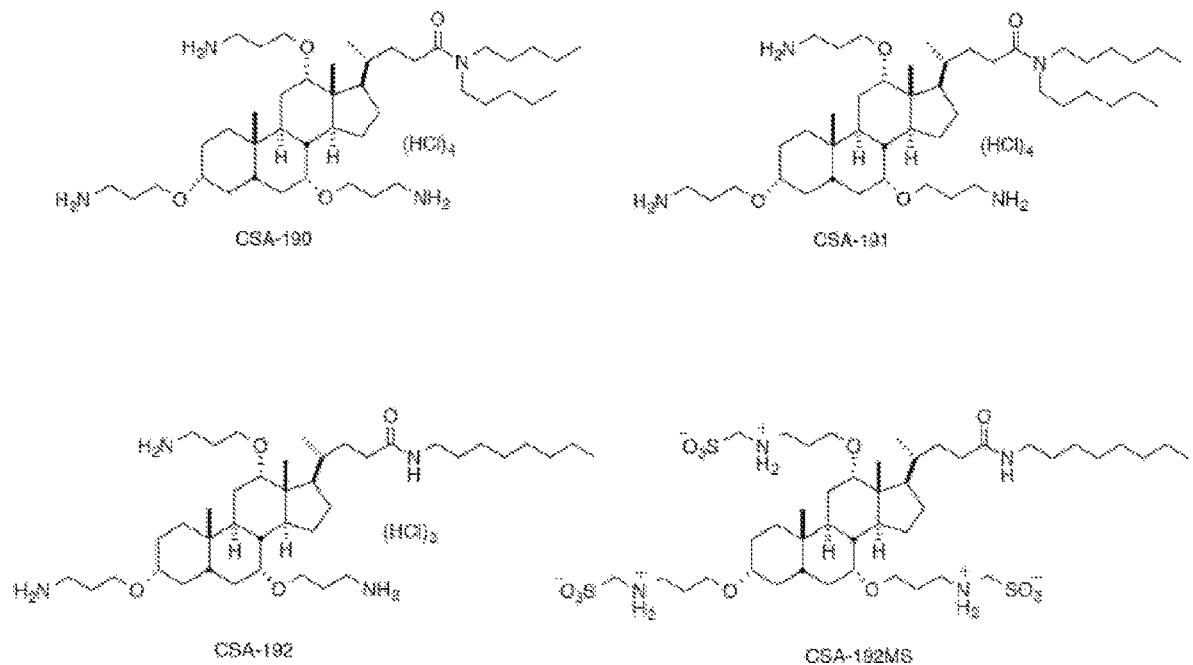
FIG. 1C illustrate example cationic steroidal antimicrobial compounds having an amide linkage included in the $R_{18}$ group.

A number of examples of CSA compounds of Formula I that can be incorporated into the dermal treatment compositions described herein are illustrated in FIGS. 1A-1C.

In addition to having antimicrobial properties, at least some CSA compounds have been shown to exhibit effective anti-swelling, anti-pain, anti-inflammatory properties. In some instances, some anti-inflammatory effects of CSA compounds may correspond to the antimicrobial effects of the CSA compounds, such as when the reduction or elimination of a microbial infection lessens a subject's inflammatory reaction against the infection. However, CSA compositions have been show n to provide anti-inflammatory effects independent of any antimicrobial effect. For example, at least some CSA compositions have been shown to be capable of reducing the inflammatory response itself. CSA compositions can also reduce pain and/or swelling.

Typically, the CSA compounds of Formula I are of two types: (1) CSA compounds having cationic groups linked to the sterol backbone with hydrolysable linkages and (2) CSA compounds having cationic groups linked to the sterol backbone with non-hydrolysable linkages. For example, one type of hydrolysable linkage is an ester linkage, and one type of non-hydrolysable linkage is an ether linkage. CSA compounds of the first type can be "inactivated" by hydrolysis of the linkages coupling the cationic groups to the sterol backbone, whereas CSA compounds of the second type are more resistant to degradation and inactivation.

In some applications, it may be desirable for a CSA compound to maintain antimicrobial, anti-inflammatory, anti-pain and/or anti-swelling effects for as long as possible. For example, some CSA compositions are contacted with dermal tissue long enough to provide ample opportunity for fouling, introduction of infection, pain, swelling, and/or inflammation. In many instances, the usable lifespan of the CSA compositions is essentially limited to how long the composition can resist fouling before becoming hazardous to the subject. Accordingly, enhancing the capability to resist microbial colonization and fouling can decrease medical care costs in addition to decreasing infection and/or inflammation risks.

In other applications, the spreading of eluted CSA compounds beyond the treatment site may be a concern. Some embodiments can be formed using an appropriate mixture of CSA compounds having hydrolysable and non-hydrolysable linkages to provide desired duration of CSA activity once the CSA compounds are exposed to biological conditions (e.g., once eluted from the treatment composition).

A number of examples of compounds of Formula I that may be used in the embodiments described herein are illustrated in FIGS. 1A-1C. Examples of CSA compounds with non-hydrolysable linkages include, but are not limited to, CSA-1, CSA-26, CSA-38, CSA-40, CSA-46, CSA-48, CSA-53, CSA-55, CSA-57, CSA-60, CSA-90, CSA-107, CSA-109, CSA-110, CSA-112, CSA-113, CSA-118, CSA-124, CSA-130, CSA-131, CSA-139, CSA-190, CSA-191 and CSA-192. Examples of CSA compounds with hydrolysable linkages include, but are not limited to CSA-27, CSA-28, CSA-29, CSA-30, CSA-31, CSA-32, CSA-33, CSA-34, CSA-35, CSA-36, CSA-37, CSA-41, CSA-42, CSA-43, CSA-44, CSA-45, CSA-47, CSA-49, CSA-50, CSA-51, CSA-52, CSA-56, CSA-61, CSA-141, CSA-142, CSA-144, CSA-145 and CSA-146. In a preferred embodiment, at least a portion of the CSA compounds incorporated into the dermal treatment compositions include CSA-131 or a salt thereof (e.g., NDSA salt). In other embodiments, the CSA compounds may include CSA-192 or a salt thereof (e.g., NDSA salt). Additional details relating to CSA compounds are described below.

In some embodiments, the one or more CSA compounds may have a structure as shown in Formula I. In Formula I, at least two of $R_3$, $R_7$, or $R_{12}$ may independently include a cationic moiety attached to the Formula I structure via a hydrolysable (e.g., an ester) or non-hydrolizable (e.g., an ether) linkage. Optionally, a tail moiety may be attached to Formula I at $R_{18}$. The tail moiety may be charged, uncharged, polar, non-polar, hydrophobic, or amphipathic, for example, and can thereby be selected to adjust the properties of the CSA and/or to provide desired characteristics.

The anti-microbial activity of the CSA compounds can be affected by the orientation of the substituent groups attached to the backbone structure. In one embodiment, the substituent groups attached to the backbone structure are oriented on a single face of the CSA compound. Accordingly, each of $R_3$, $R_7$, and $R_{12}$ may be positioned on a single face of Formula I. In addition, $R_{18}$ may also be positioned on the same single face of Formula I.

In some embodiments, one or more CSA compounds are included by weight of the treatment composition at about 0.1%, 0.5%, 1%, 3%, 5%, 10%, 15%, 20%, 25%, or 30% or are included by weight within a range defined by any two of the foregoing values.

Another advantageous characteristic associated with one or more of the CSA compounds described herein is their effectiveness in killing biofilm type bacteria, in addition to planktonic bacteria. Many other anti-microbial agents suitable for application to a live subject, including nearly all antibiotics, have limited effectiveness in killing bacteria present in a biofilm form. This is believed to be due to the fact that most of such antibiotics attack enzymes associated with growth of bacteria. Biofilm bacteria are believed to be in something of a sessile state so that the targeted growth enzymes are not being produced. This results in the biofilm bacteria surviving an antibiotic treatment, meaning they are capable of continuing to pose a pathogenic threat even after treatment with such antibiotics. CSA compounds operate through a different mechanism, which is effective against both planktonic and biofilm type bacteria.

In preferred embodiments, CSA compounds used herein are provided in salt form. It has been found that certain salt forms of CSAs exhibit beneficial properties such as improved solubility characteristics, crystallinity, flow, and storage stability. Some embodiments are directed to a sulfuric acid addition salt or sulfonic acid addition salt of a CSA. In some embodiments, the sulfonic acid addition salt is a disulfonic acid addition salt. In some embodiments, the sulfonic acid addition salt is a 1,5-naphthalenedisulfonic acid (NDSA) addition salt, such as an NDSA salt of CSA-131 and/or an NDSA salt of CSA-192. In some embodiments, the acid addition salt is a mono-addition salt. In other embodiments, the acid addition salt is a di-addition salt (i.e., to form a bis-naphthalene disulfonate salt) or tri-addition salt. In other embodiments, the acid addition salt is a tetra-addition salt.

II. Dermal Treatment Compositions Incorporating CSA Compounds

As used herein, a "dermal treatment composition" refers to a treatment composition that may be injected or introduced into and/or applied onto a subject's dermal tissues. Typically, such a treatment composition is used under circumstances in which biological compatibility is of concern (e.g., because infection and/or inflammation can result). Some treatment compositions are injectable or otherwise used subcutaneously. It will be understood that some treatment compositions need not be fully injected within a subject's body, however. For example, in some applications, a treatment composition may be applied to outer or exposed dermal tissue (e.g., a tissue glue for wound closure purposes).

Non-limiting examples of treatment compositions which may incorporate one or more CSA compounds include soft tissue fillers (which are also referred to as dermal fillers), tissue glues (which may also be referred to as tissue adhesives, dermal glues, and the like), botox, dermal implants, and other treatment compositions that may be injected into or applied onto a dermal tissue treatment site. Soft tissue fillers are typically provided as a gel, paste, or similarly viscous form. Tissue glue compositions may have varying pre-set viscosities and consistencies, depending on desired application, which then solidify upon setting of the glue composition. Injectable botox compositions containing botox and CSA compound can have the same or similar fluidity as conventional botox compositions. Other injectable compositions that can incorporate a CSA compound include collagen compositions used to cosmetically and/or functionally enhance the size and/or shape of body parts, such as lip, breast, buttock, chest, calf, or genital augmentation, plastic surgery, labiaplasty, and the like.

In some embodiments, a soft tissue filler composition includes one or more bioabsorbable filler substances, such as collagen, hyaluronic acid, hydroxyapatite minerals (e.g., calcium hydroxyapatite), poly-l-lactic acid (PLLA), other bioabsorbable filler materials, or combinations thereof. In some embodiments, a soft tissue filler composition includes one or more non-bioabsorbable filler materials, such as silicone, polymethylmethacrylate, biocompatible polymers, other biocompatible materials, or combinations thereof.

In some embodiments, the treatment compositions as described herein effectively provide inherent antimicrobial activity that minimizes sterilization requirements as compared to other treatment compositions not including CSA compounds. Nevertheless, the treatment compositions, in particular dermal filler embodiments, may be sterilized in a variety of ways, such as by autoclaving, using a gaseous species, or irradiation.

A dermal filler composition may be placed in filled syringes and the syringes sterilized by an autoclave process using suitable temperature, pressure, time, and moisture settings as is known in the art. Autoclaving can be accomplished by applying a mixture of heat, pressure and moisture to the treatment composition being sterilized. Many different sterilization temperatures, pressures and cycle times can be used. For example, filled syringes may be sterilized at a temperature of about 120° C. to about 130° C., or greater. Moisture may or may not be utilized. The pressure applied may depend on the temperature used in the sterilization process. The sterilization cycle may have a duration of about 1 minute to about 20 minutes, or more.

Another method of sterilization incorporates the use of a gaseous species that is known to kill or eliminate transmissible agents. In some embodiments, ethylene oxide can be used as a sterilization gas and is known in the art to be useful in sterilizing medical devices and products.

A further method of sterilization incorporates the use of an irradiation source known in the art to kill or eliminate transmissible agents. A beam of irradiation is targeted at the syringe containing a dermal treatment composition, such as a dermal filler containing HA, and the wavelength of energy kills or eliminates the unwanted transmissible agents. Useful energy includes, but is not limited to, ultraviolet (UV) light, gamma irradiation, visible light, microwaves, or any other wavelength or band of wavelengths which kills or eliminates the unwanted transmissible agents, preferably without substantially altering of degrading the composition.

In some embodiments, a tissue glue composition includes an adhesive component provided in a liquid, gel, or paste form to enable application of the tissue glue to a treatment site where setting can occur. In preferred embodiments, the adhesive includes cyanoacrylate monomers configured to polymerize upon application to the treatment site. In more preferred embodiments, the cyanoacrylate is an octyl or butyl ester of cyanoacrylate, such as octyl cyanoacrylate, n-butyl cyanoacrylate, isobutyl cyanoacrylate, or combination thereof. In some embodiments, the adhesive component includes one or more additional agents, such as one or more bonding agents, viscosity adjustors, polymerization accelerators (e.g., alcohols and/or basic compounds such as bicarbonate salts or amines) or retardants (e.g., hydroquinone, acids, and/or other reducing agents). One or more tissue glue embodiments described herein may be utilized for closing wounds (e.g., lacerations, surgical incisions, cuts, etc.), embolizing blood vessels, and/or occluding fistulas, alone or in combination with a dermal filler.

The dermal treatment compositions described herein incorporate one or more CSA compounds to provide enhanced antimicrobial, anti-inflammatory, analgesic, anti-pain anti-swelling and/or wound healing effects. For example, one or more CSA compounds may be mixed with an adhesive and/or filler component to form the integrated CSA composition prior to injection or application of the composition. In this manner, a reservoir of CSA compounds resides in the composition after injection or application at the treatment site and is able to provide extended activity at the treatment site.

For example, a tissue glue incorporating one or more CSA compounds, once injected and/or applied, will form a tissue seal/plug having a reservoir of CSA compounds directly incorporated into and distributed within the structure of the tissue seal/plug. In another example, a soft tissue filler (e.g., a hyaluronic acid gel) incorporating one or more CSA compounds, once injected, can form a bolus having a reservoir of CSA compounds directly incorporated into and distributed within the matrix of the filler material.

Any of the CSA compounds described herein may be used in an implantable or injectable treatment composition. In some embodiments, one or more CSA compounds are included in a salt form. Preferred salt forms include sulfuric acid addition salts or sulfonic acid addition salts, including NDSA addition salts such as 1,5-NDSA addition salts. These and other salt forms of CSAs have shown beneficial properties such as good flowability/mixability, good storage stability, and solubility profiles beneficial for time-release applications.

In particular, such salt forms of CSAs are useful for mixing with treatment compositions such as soft tissue fillers, tissue glues, botox, injectable and/or subcutaneous compositions, and the like. The compositions thereby have CSA compounds included within the structure of the composition after injection and/or application. Some salt forms of CSA compounds have been shown to have limited or no interaction with treatment compositions when mixed, leaving the CSA compounds in an active form capable of providing enhanced antimicrobial and/or anti-inflammatory functionality at the dermal tissue treatment site after injection and/or application of the treatment compositions.

In some embodiments, one or more CSA compounds are included in a concentration in a range of about 0.1% to about 30% (w/w), or about 1% to about 20% (w/w), or about 3% to about 15% (w/w), or about 5% to about 10% (w/w) of the treatment composition. In some embodiments, an amount of one or more CSA compounds is added to provide desired anti-microbial effects, anti-inflammatory effects, analgesic effects, and/or tissue wound healing effects upon injection and/or application of the treatment composition at a treatment site. For example, an effective amount may be an amount within the foregoing ranges. In addition, in some implementations, CSAs may provide effective anti-microbial, anti-inflammatory, analgesic, and/or tissue wound healing functionality even at concentrations of about 5% (w/w) or less, 3% (w/w) or less, or about 1% (w/w) or less.

Treatment compositions described herein can provide a variety of benefits. For example, treatment compositions can be used more extensively or with longer durations as a result of reductions in fouling and biofilm formation. One or more of the disclosed embodiments can reduce the occurrence of treatment-related infections, and thereby reduce the need for treatment with antibiotics or other antimicrobials. Furthermore, the antimicrobial effects of such treatment compositions limit or reduce the need for prophylactic antibiotic administration. For example, antibiotics are typically administered prophylactically when wound closures are made using conventional tissue glues. Utilization of a tissue glue having one or more incorporated CSA compounds, as described herein, may reduce or eliminate the need to administer such prophylactic antibiotics. CSA compounds have also been shown to provide anti-inflammatory, anti-pain, and/or anti-swelling effects and/or accelerated rate of tissue wound healing independent of any corresponding antimicrobial effects.

III. Methods of Manufacturing Dermal Treatment Compositions

In some embodiments, a method of manufacturing a dermal treatment composition having one or more incorporated CSA compounds comprises: (1) providing a biologically compatible material suitable for application onto or injection into dermal tissue; and (2) mixing one or more CSA compounds with the biologically compatible material.

In some embodiments, the one or more CSA compounds are provided in salt form. In preferred embodiments, the one or more CSA compounds are provided in the form of a sulfonic acid addition salt, including disulfonic addition salts such as NDSA salts. Such salt forms have shown to be flowable and readily mixable with materials forming the treatment compositions. In addition, such salt forms have been shown to have beneficial solubility profiles and/or to not react with or lose activity upon mixing with the materials of the treatment compositions, thereby preserving the effectiveness of the CSA compounds in providing antimicrobial, anti-inflammatory, analgesic, anti-swelling and/or accelerated tissue healing properties.

In some embodiments, the one or more CSA compounds are provided in a solid salt form. In some embodiments, solid form CSA compounds are processed to a desired average particle size prior to mixing with the treatment compositions, such as through a micronizing process using one or more impact mills (e.g., hammer mills, jet mills, and/or ball, pebble, or rod mills) or other suitable processing units. After sizing, the solid form CSA compounds will preferably have an average particle size of about 50 nm, 100 nm, 150 nm, 250 nm, 500 nm, 1 µm, or an average particle size within a range defined by any two of the foregoing values.

Treatment compositions incorporating one or more CSA compounds are particularly beneficial in applications in which the treatment composition is intended to be in biological contact with a subject for relatively long periods of time and/or where microbial colonization and fouling is a likely problem. Certain embodiments incorporating one or more CSA compounds within the structure of the treatment composition (e.g., within a soft tissue filler bolus or a tissue seal/plug) have shown efficacy lasting at least about a month, with efficacy expected to endure for several months. In some applications, this is beyond the intended or needed life of the composition itself. For example, efficacy may endure longer than the time needed for a tissue wound to close or longer than the time needed for a bolus of temporary soft tissue filler to be absorbed.

In some embodiments, the treatment composition can includes silicone. Silicone has shown good mixability with at least some of the CSA compounds disclosed herein, with no indication of the silicone reacting with or reducing the activity of the CSA compounds.

IV. Methods of Using a Dermal Treatment Composition

One or more embodiments are directed to methods of controlling microbial growth, including biofilm growth, on a treatment composition and/or at a treatment site at which the dermal treatment composition has been injected and/or applied. In some embodiments, a method comprises: (1) providing a dermal treatment composition having one or more CSA compounds, (2) injecting and/or applying the dermal treatment composition at a dermal tissue treatment site; and (3) the dermal treatment composition killing one or more microbes contacting the treatment composition. The treatment composition may be effective in killing a wide variety of microbes. In some embodiments, the method provides enhanced protection from biofouling and/or associated infection (e.g., as compared to a similar treatment composition not incorporating CSA compounds).

In some applications, a treatment composition may be delivered to interior (e.g., subdermal) tissues. In some applications, a treatment composition may be applied to an outer dermal surface (e.g., for closure of a shallow skin wound).

One or more embodiments are directed to methods of reducing inflammation, pain and/or swelling at a treatment site at which a treatment composition is injected or applied. In some embodiments, a method comprises: (1) providing a dermal treatment composition having one or more CSA compounds, (2) injecting and/or applying the treatment composition at a dermal tissue treatment site; and (3) the dermal treatment composition reducing or preventing inflammation, pain and/or swelling at the treatment site (e.g., as compared to a similar treatment composition not incorporating CSA compounds).

One or more embodiments are directed to methods of increasing the rate of tissue healing at an implantation site at which a medical device has been implanted. In some embodiments, a method comprises: (1) providing a dermal treatment composition having one or more incorporated CSA compounds, (2) injecting and/or applying the treatment composition at a targeted treatment site; and (3) the treatment composition increasing the rate of tissue healing at the treatment site (e.g., as compared to a similar treatment composition not incorporating CSA compounds).

One or more of the methods described herein may be utilized to prevent or reduce conditions associated with high serum levels of inflammatory cytokines, such as IL-6, TNF alpha, and others. These levels can rise rapidly following surgical procedures. CSA compounds have been shown to dampen or reduce the inflammatory response. Further, CSA compounds may promote faster healing and regeneration of traumatized tissue, thereby more quickly reducing pathways through which inflammatory cytokines can pass into systemic circulation to cause or aggravate associated medical condition(s). CSA-compounds can provide analgesic properties, such as by modulating $P2X_7$ receptors associated with pain.

In some embodiments, the CSA compounds in dermal treatment compositions maintain efficacy (for killing microbes, preventing or reducing inflammation, pain and/or swelling and/or accelerating wound healing) for at least 4 days after injection/application, at least 7 days after injection/application, at least 14 days after injection/application, at least 30 days after injection/application, at least 60 days after injection/application, or about 90 days after injection/application. In some embodiments, the treatment composition maintains efficacy for as long as the treatment composition (e.g., dermal filler bolus or tissue seal/plug) resides at the treatment site (e.g., about a week, about two weeks, about a month, about 2 or 3 months).

V. EXAMPLES

Example 1

To determine the role of synthetic ceragenins CSA-13, 44 and 90 in treating or reducing inflammation, mesenchymal stem cells (MSC), targeted mRNA panels from SABiosciences, and primary cells from Lonza were selected and utilized. Cells were purchased from Lonza.com and used fresh for each test using recommended media and culture conditions.

After treatment, mRNA was isolated using Qiagen RNeasy Mini Kit®, and quantified using a NanoDrop 2000® by UV at 260 nm and 260/280 ratio for purity. cDNA was made using a First Strand Kit® from SABiosciences and processed for real time PCR using a kit from the same company for selected analysis of wound healing pathways. Results from q-PCR were uploaded to the SABiosciences site and to Ingenuity.com web site for analysis and pathway mapping.

On day 1, primary human MSC cells were plated at 200,000 cells/well using 6-well plates with 3 ml of recommended media—hMSC Basal Medium+BulletKit (50 ml Growth Supplement, 10 ml L-glutamine, and 0.5 ml gentamicin sulfate amphotercin-B) for 24 hours. Only early passages of cells were used, and never from frozen stock.

On day 2, cells were treated with compounds dissolved in DMSO diluted 1:1000 or more to avoid effects of the solvent. The final testing concentration for CSA-13 was 5.0 µM. Treatment lasted 8 hours and was followed by RNA isolation using QIAGEN RNeasy Mini Kit® (74104). RNA was measured at 260/280 nm using a NanoDrop 2000® and normalized to 2.4 ng per well, cDNA preparation was done using QIAGEN First Strand kit 330401. q-PCR was run as absolute quantification and threshold set at 0.1 units. Dendritic cells were plated at 500,000 cells/well using 24-well plate with 500 µl of Lonza LGM-3 Complete Growth Medium with and without compound. Treatment lasted 8 hours and was followed by RNA isolation using QIAGEN RNeasy Mini Kit® (74104). RNA was measured at 260/280 nm using NanoDrop2000® and normalized to 2.4 ng per well, cDNA preparation was done using QIAGEN First Strand kit 330401. PCR was run as absolute quantification and threshold set at 0.1 units.

The results of these experiments are summarized in Tables 1-3 for CSA-13, 44, and 90, respectively. The results highlight the significant modulation of genes related to inflammation, such as IL1A (Interleukin-1 alpha), IL1B (Interleukin-1 beta), TLR2 (Toll-like receptor 2), TLR4 (Toll-like receptor 4), TLR6 (Toll-like receptor 6), TLR8 (Toll-like receptor 8), TLR9 (Toll-like receptor 9), TNF (Tumor necrosis factor), TNFRSF1A (Tmor necrosis factor receptor superfamily member 1A), IRAK2 (Interleukin-1 receptor-associated kinase 2), NFKB1 (Nuclear factor of kappa light polypeptide gene enhancer in B-cells 1), NFKB2 (Nuclear factor of kappa light polypeptide gene enhancer in B-cells 2), and NFKBIA (Nuclear factor of kappa light polypeptide gene enhancer in B-cells inhibitor, alpha). Such results clearly illustrate the potential of CSAs for modulating inflammation.

TABLE 1

Gene Expression Results for CSA-13

| Gene Symbol | Fold Regulation |
| --- | --- |
| IL1A | −5.5237 |
| IL1B | −16.3901 |
| TLR2 | −7.6418 |
| TLR4 | −2.6139 |
| TLR6 | −4.8417 |
| TLR8 | −2.107 |
| TLR9 | −2.1421 |
| TNF | −8.1805 |
| TNFRSF1A | −5.1031 |
| IRAK2 | −43.5175 |
| NFKB1 | −3.4437 |
| NFKB2 | −4.2155 |
| NFKBIA | −22.966 |

TABLE 2

Gene Expression Results for CSA-44

| Gene Symbol | Fold Regulation |
| --- | --- |
| IL1A | −6.0325 |
| IL1B | −28.5329 |
| IRAK2 | −31.8021 |
| NFKB1 | −3.2891 |
| NFKB2 | −2.2766 |
| NFKBIA | −52.206 |
| TLR2 | −15.7179 |
| TLR4 | −2.977 |
| TLR6 | −2.392 |
| TLR8 | −8.2256 |

TABLE 2-continued

Gene Expression Results for CSA-44

| Gene Symbol | Fold Regulation |
| --- | --- |
| TLR9 | −1.8905 |
| TNF | −25.9588 |
| TNFRSF1A | −2.2461 |

TABLE 3

Gene Expression Results for CSA-90

| Gene Symbol | Fold Regulation |
| --- | --- |
| IL1A | −6.96 |
| 1L1B | −3.6734 |
| IRAK2 | −52.0069 |
| NFKB1 | −4.718 |
| NFKB2 | −2.5474 |
| NFKBIA | −26.0352 |
| TLR2 | −13.6933 |
| TLR4 | −3.4278 |
| TLR6 | −2.0885 |
| TLR8 | −4.1972 |
| TLR9 | −1.8613 |
| TNF | −4.8514 |
| TNFRSF1A | −7.3196 |

Example 2

IL-6 is a marker of systemic inflammation. Female C57/BL6 mice were infected in the respiratory tract with a non-lethal dose of *P. aeruginosa* as a model of pneumonia. One cohort (n=6) also received 80 mg/kg CSA-13; a second cohort (n=6) also received 40 mg/kg CSA-13; a third (n=6) received no CSA treatment; and a fourth (n=6) was not infected. Examination of IL-6 levels in the kidneys 24 hours post-infection demonstrated that those infected animals not treated with CSA had IL-6 levels >15 times those of control and 5-10 times higher than those of the CSA-treated animals. Thus, treatment with CSA significantly reduced kidney IL-6 levels in a pneumonia model.

Example 3

CSA-131 (bis-DNS salt) was used in this Example. This material is a stable, colorless solid and is insoluble in cyanoacrylate. To ensure uniform distribution of CSA-131 in the cyanoacrylate polymer, the solid was micronized using a jet mill to give an average particle size of 200 nm. The resulting powder was added to cyanoacrylate to give a 5% (w/w) mixture, which was vigorously agitated. No immediate change in viscosity was observed, and the mixture remained non-viscous for more than 15 min.

The substrate onto which the CSA-131-cyanoacrylate mixture was applied was small (4 mm i.d., 5 mm length) PVC tubes. This substrate was chosen because it had been used previously to evaluate antimicrobial efficacy of ceragenins eluting from polymers. Tubes were "skewered" on 22 gauge needles to allow efficient manipulation.

Tubes were immersed in the CSA-131-cyanoacrylate mixture described above with a residence time of 15 sec. The applied glue was then allowed to polymerize with the tubes on a vertical rotating wheel to encourage even distribution of the glue. Weight differences were used to gauge the thickness of the applied glue, and films were calculated to be between 100 and 200 microns. The applied glue was allowed to polymerize for a minimum of 1 h before evaluation, by which point the coatings were mechanically stable. Controls were prepared by immersing tubes in cyanoacrylate lacking CSA-131.

Efficacy of incorporated CSA-131 in preventing bacterial colonization was tested using *Staphylococcus aureus* in a nutrient medium (10% tryptic soy broth in phosphate buffered saline). Aliquots (1 mL) of the medium were inoculated with *S. aureus* ($10^6$ CFU), and the coated tubes were immersed in the medium. The tubes were incubated at 37° C. for 24 hours, after which growth was evaluated in the medium. From previous experiments, the inventors established that if growth is not supported in the medium the device is not colonized by bacteria. And the converse is true: if growth is supported in the medium then the device is colonized, at least to some extent.

After 24 hours of incubation, control tubes (cyanoacrylate coated without CSA-131; Cont. 1-Cont. 3 in Table 4 below) were colonized with ca. $10^7$ CFU/cm$^2$ adhered to the tubes. In contrast, tubes coated with cyanoacrylate containing CSA-131 (A-C in Table 4 below) remained un-colonized. These tubes were then added to fresh media inoculated and incubated for 24 h. This process was repeated every 24 h until growth was supported in the growth medium. Only after seven days was growth observed. Results are tabulated in Table 4, which shows the duration of activity of the cyanoacrylate films. The label "N" indicates lack of bacterial growth, and "G" indicates bacterial growth.

TABLE 4

Tissue Glue vs. *S. aureus*

| | Day 1 | Day 2 | Day 3 | Day 4 | Day 5 | Day 6 | Day 7 | Day 8 |
| --- | --- | --- | --- | --- | --- | --- | --- | --- |
| A | N | N | N | N | N | N | G | G |
| B | N | N | N | N | N | N | G | G |
| C | N | N | N | N | N | N | G | G |
| Cont. 1 | G | G | G | G | G | G | G | G |
| Cont. 2 | G | G | G | G | G | G | G | G |
| Cont. 3 | G | G | G | G | G | G | G | G |

Example 4

Example 4 followed the protocol of Example 3, except that the CSA-131 micronized powder was added to cyanoacrylate to give a 10% (w/w) mixture, and the efficacy of the resulting tissue glue films was tested against *Escherichia coli* (O157) in a nutrient medium (10% tryptic soy broth in phosphate buffered saline). As in Example 3, Aliquots (1 mL) of the medium were inoculated with $10^6$ CFU of the test microbe, and the coated tubes were immersed in the medium. Also as in Example 3, growth medium was exchanged every 24 hours. Results are tabulated in Table 5, where "N" indicates no growth and "G" indicates growth.

TABLE 5

Tissue Glue vs. *E. coli*

| | Day 1 | Day 2 | Day 3 | Day 4 | Day 5 |
| --- | --- | --- | --- | --- | --- |
| A | N | N | N | N | G |
| B | N | N | N | N | G |
| C | N | N | N | N | G |

The results of Examples 3 and 4 demonstrate that cyanoacrylate films can be readily colonized by bacteria and that colonization occurs rapidly. In other words, cyanoacrylates provide no antimicrobial activity but can provide a locale for bacteria to flourish. CSA-131 eluting from cyanoacrylate films prevented bacterial colonization for both test organisms. Example 4 included 10% CSA-131; however, it is apparent that lower percentages would provide the desired antimicrobial activities. As shown, the percentage of CSA-131 in Example 3 at 5% also proved effective. It is anticipated that duration of activity will be comparable for these and similar ranges. The assay for effectiveness used is rigorous because the coating is fully immersed in a growth medium into which the ceragenin can freely elute. Furthermore, regular exchange of growth medium and re-inoculation provides repeated opportunities for bacteria to establish biofilm on the tubes.

Example 5

A rabbit intracutaneous reactivity test according to ISO-10933-10 (as the standard existed in January 2017) was performed comparing a dermal filler product without integrated CSA compound to a dermal filler product including integrated CSA-131. The rabbit which was administered the dermal filler including CSA-131 showed an inflammation score of 1 for all 3 days of testing. No toxicity or adverse effects were observed. By way of comparison, the Juvederm Voluma™ hyaluronic acid based injectable dermal filler (available from Allergan) was reported as failing the intracutaneous reactivity test at the 3 day time period and only achieved a "non-irritant" score by extending the time frame to 14 days. See U.S. Food and Drug Administration's "Summary of Safety and Effectiveness Data (SSED)" for Juvederm Voluma XC, Premarket Approval Application (PMA) No. P110033, pg. 5, Table 2.

Example 6

Several CSA compounds were tested against *Pseudomonas aeruginosa* and *Staphylococcus aureus* mixed-species biofilms grown for an initial 22 hours and subjected to 20 hours of treatment. Many CSA compounds showed more potent anti-biofilm activity than the classical antimicrobial peptide (AMP) LL-37. Table 6 shows minimum inhibitory concentrations (MIC) and minimum bactericidal concentrations (MBC) of LL-37 for the various CSA compounds against the mixed-species biofilms.

TABLE 6

|  | P. aeruginosa (µg/ml) | | S. aureus (µg/ml) | |
| --- | --- | --- | --- | --- |
|  | MIC | MBC | MIC | MBC |
| LL-37 | >200 | >200 | >200 | >200 |
| CSA-8 | 25 | 100 | 3.125 | 6.25 |
| CSA-11 | >200 | >200 | 50 | 50 |
| CSA-13 | 3.125 | 6.25 | 0.78 | 0.78 |
| CSA-25 | 25 | 50 | 1.56 | 3.25 |
| CSA-44 | 3.125 | 6.25 | 1.56 | 3.25 |
| CSA-54 | 50 | 100 | 6.25 | 25 |
| CSA-90 | 6.25 | 6.25 | 1.56 | 1.56 |
| CSA-192 | 3.125 | 6.25 | 0.78 | 1.56 |
| CSA-131 | 3.125 | 3.125 | 0.78 | 1.56 |
| CSA-134 | 12.5 | 25 | 0.78 | 3.125 |
| CSA-138 | 3.125 | 6.25 | 1.56 | 3.125 |
| CSA-142 | 3.125 | 3.125 | 3.125 | 3.125 |
| CSA-144 | 12.5 | 50 | 3.125 | 3.125 |
| CSA-145 | 12.5 | 50 | 3.125 | 3.125 |

Example 7

CSA-131 was tested in vitro against a set of clinical isolates representing bacterial species commonly associated with hospital-acquired infections. Antimicrobial susceptibility testing for 74 clinical isolates was performed. Broth microdilution using frozen-form MIC panels consisted of three media types: cation-adjusted Mueller-Hinton broth (CA-HMB), CA-HMB supplemented with 2.5-5% lysed horse blood for *S. pneumoniae* and *Haemophilus* test media (HTM) for *Haemophilus* spp. Results are shown in Table 7.

TABLE 7

| Organisms (No. tested) | No. of isolates at MIC (cumulative % inhibited) | | | $MIC_{50}$ | $MIC_{90}$ |
| --- | --- | --- | --- | --- | --- |
|  | 2 µg/ml | 4 µg/ml | 8 µg/ml | | |
| All (74) | 23 (31.1%) | 40 (85.1%) | 11 (100%) | 4 | 8 |
| *Staphylococcus aureus* (10) | 10 (100%) | 0 (100%) | 0 (100%) | 2 | 2 |
| *Streptococcus Pneumoniae* (10) | 0 (0%) | 10 (100%) | 0 (100%) | 4 | 4 |
| *Haemophilus* spp.[a] (10) | 0 (0%) | 0 (0%) | 10 (100%) | 8 | 8 |
| *Enterobacteriaceae*[b] (22) | 4 (18.2%) | 18 (100%) | 0 (100%) | 4 | 4 |
| Non-fermenters[c] (22) | 9 (40.9%) | 12 (95.5%) | 1 (100%) | 4 | 4 |

[a]includes 8 *H. influenza* and 2 *H. parainfluenzae*
[b]includes 5 *E. aerogenes*, 5 *E. cloacae* species complex, 2 *E. coli* and 10 *K. pneumoniae*
[c]includes 10 *A. baumannii* species complex, 10 *P. aeruginosa* and 2 *S. maltophilia*

VI. Additional Details Of CSA Compounds

More specific examples of CSA compounds according to Formula I are shown below in Formulas II and III, wherein Formula III differs from Formula II by omitting $R_{15}$ and the ring carbon to which it is attached. The R groups shown in the Formulae can have a variety of different structures. CSA compounds, and a variety of different R groups, useful in accordance with the present disclosure, are disclosed in U.S. Pat. Nos. 6,350,738, 6,486,148, 6,767,904, 7,598,234, 7,754,705, 8,975,310 and 9,434,759, which are incorporated herein by reference.

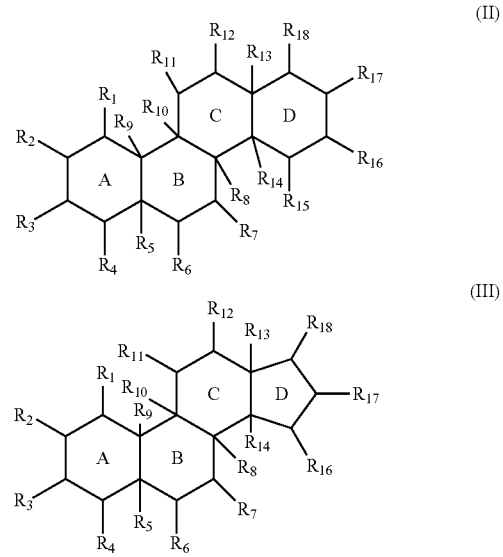

In some embodiments of Formulas II and III, at least two of $R_3$, $R_7$, and $R_{12}$ may independently include a cationic moiety (e.g., amino or guanidino groups) bonded to the steroid backbone structure via a non-hydrolysable or hydrolysable linkage. For the embodiments of the present disclosure, the linkage is preferably non-hydrolysable under conditions of sterilization and storage, and physiological conditions. Such cationic functional groups (e.g., amino or guanidino groups) may be separated from the backbone by at least one, two, three, four or more atoms.

Optionally, a tail moiety may be attached to the backbone structures at $R_{18}$. The tail moiety may have variable chain length or size and may be charged, uncharged, polar, non-polar, hydrophobic, amphipathic, and the like. The tail moiety may be configured, for example, to alter the hydrophobicity/hydrophilicity of the ceragenin compound. CSA compounds having different degrees of hydrophobicity/hydrophilicity may, for example, have different rates of uptake into different target microbes.

The R groups described herein, unless specified otherwise, may be substituted or unsubstituted.

In some embodiments shown by Formulas II and III:
each of fused rings A, B, C, and D may be independently saturated, or may be fully or partially unsaturated, provided that at least two of A, B, C, and D is saturated, wherein rings A, B, C, and D form a ring system. Other ring systems can also be used, e.g., 5-member fused rings and/or compounds with backbones having a combination of 5- and 6-membered rings;

$R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, alkyl, hydroxyalkyl, alkyloxyalkyl, alkylcarboxyalkyl, alkylaminoalkyl, alkylaminoalkylamino, alkylaminoalkylamino-alkylamino, aminoalkyl, aryl, arylaminoalkyl, haloalkyl, alkenyl, alkynyl, oxo, a linking group attached to a second steroid, aminoalkyloxy, aminoalkyloxyalkyl, aminoalkylcarboxy, aminoalkylaminocarbonyl,aminoalkylcarboxamido, di(alkyl)aminoalkyl, $H_2N$—$HC(Q_5)$-C(O)—O—, $H_2N$—$HC(Q_5)$-C(O)—N(H)—, azidoalkyloxy, cyanoalkyloxy, P.G.-HN—$HC(Q_5)$-C(O)—O—, guanidinoalkyloxy, quaternary ammonium alkylcarboxy, and guanidinoalkyl carboxy, where $Q_5$ is a side chain of any amino acid (including a side chain of glycine, i.e., H), and P.G. is an amino protecting group; and $R_5$, $R_8$, $R_9$, $R_{10}$, $R_{13}$, $R_{14}$ and $R_{18}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, alkyl, hydroxyalkyl, alkyloxyalkyl, aminoalkyl, aryl, haloalkyl, alkenyl, alkynyl, oxo, a linking group attached to a second steroid, aminoalkyloxy, aminoalkylcarboxy, aminoalkylaminocarbonyl, di(alkyl)aminoalkyl, $H_2N$—$HC(Q_5)$-C(O)—O—, $H_2N$—$HC(Q_5)$-C(O)—N(H)—, azidoalkyloxy, cyanoalkyloxy, P.G.-HN—$HC(Q_5)$-C(O)—O—, guanidinoalkyloxy, and guanidinoalkyl-carboxy, where $Q_5$ is a side chain of any amino acid, P.G. is an amino protecting group.

In some embodiments, at least one, and sometimes two or three of $R_{1-4}$, $R_6$, $R_7$, $R_{11}$, $R_{12}$, $R_{15}$, $R_{16}$, $R_{17}$, and $R_{18}$ are independently selected from the group consisting of aminoalkyl, aminoalkyl oxy, alkyl carboxyalkyl, alkyl aminoalkyl amino, alkyl aminoalkyl-aminoalkylamino, aminoalkylcarboxy, arylaminoalkyl, aminoalkyloxyaminoalkylamino-carbonyl, aminoalkylaminocarbonyl, aminoalkyl-carboxamido, a quaternary ammonium alkylcarboxy, di(alkyl) aminoalkyl, $H_2N$—$HC(Q_5)$-C(O)—O—, $H_2N$—$HC(Q_5)$-C(O)—N(H)—, azidoalkyloxy, cyanoalkyloxy, P.G.-HN—$HC(Q_5)$-C(O)—O—, guanidine-alkyl oxy, and guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, $(C_1$-$C_{22})$ alkyl, $(C_1$-$C_{22})$ hydroxyalkyl, $(C_1$-$C_{22})$ alkyloxy-$(C_1$-$C_{22})$ alkyl, $(C_1$-$C_{22})$ alkylcarboxy-$(C_1$-$C_{22})$ alkyl, $(C_1$-$C_{22})$ alkylamino-$(C_1$-$C_{22})$ alkyl, $(C_1$-$C_{22})$ alkylamino-$(C_1$-$C_{22})$ alkylamino, $(C_1$-$C_{22})$ alkylamino-$(C_1$-$C_{22})$ alkylamino- $(C_1$-$C_{22})$ alkylamino, $(C_1$-$C_{22})$ aminoalkyl, aryl, arylamino-$(C_1$-$C_{22})$ alkyl, $(C_1$-$C_{22})$ haloalkyl, $C_2$-$C_6$ alkenyl, $C_2$-$C_6$ alkynyl, oxo, a linking group attached to a second steroid, $(C_1$-$C_{22})$ aminoalkyloxy, $(C_1$-$C_{22})$ aminoalkyloxy-$(C_1$-$C_{22})$ alkyl, $(C_1$-$C_{22})$ aminoalkylcarboxy, $(C_1$-$C_{22})$ aminoalkylaminocarbonyl, $(C_1$-$C_{22})$ aminoalkyl-carboxamido, di$(C_1$-$C_{22}$ alkyl)aminoalkyl, $H_2N$—$HC(Q_5)$-C(O)—O—, $H_2N$—$HC(Q_5)$-C(O)—N(H)—, $(C_1$-$C_{22})$ azidoalkyloxy, $(C_1$-$C_{22})$ cyanoalkyloxy, P.G.-HN—$HC(Q_5)$-C(O)—O—, $(C_1$-$C_{22})$ guanidinoalkyloxy, $(C_1$-$C_{22})$ quaternary ammonium alkylcarboxy, and $(C_1$-$C_{22})$ guanidinoalkyl carboxy, where $Q_5$ is a side chain of an amino acid (including a side chain of glycine, i.e., H), and P.G. is an amino protecting group; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, $(C_1$-$C_{22})$ alkyl, $(C_1$-$C_{22})$ hydroxyalkyl, $(C_1$-$C_{22})$ alkyloxy-$(C_1$-$C_{22})$ alkyl, $(C_1$-$C_{22})$ aminoalkyl, aryl, $(C_1$-$C_{22})$ haloalkyl, $(C_2$-$C_6)$ alkenyl, $(C_2$-$C_6)$ alkynyl, oxo, a linking group attached to a second steroid, $(C_1$-$C_{22})$ aminoalkyloxy, $(C_1$-$C_{22})$ aminoalkylcarboxy, $(C_1$-$C_{22})$ aminoalkylaminocarbonyl, di$(C_1$-$C_{22}$ alkyl)aminoalkyl, $H_2N$—$HC(Q_5)$-C(O)—O—, $H_2N$—$HC(Q_5)$-C(O)—N(H)—, $(C_1$-$C_{22})$ azidoalkyloxy, $(C_1$-$C_{22})$ cyanoalkyloxy, P.G.-HN—$HC(Q_5)$-C(O)—O—, $(C_1$-$C_{22})$ guanidinoalkyloxy, and $(C_1$-$C_{22})$ guanidinoalkylcarboxy, where Q5 is a side chain of any amino acid, and P.G. is an amino protecting group;

provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of $(C_1$-$C_{22})$ aminoalkyl, $(C_1$-$C_{22})$ aminoalkyloxy, $(C_1$-$C_{22})$ alkylcarboxy-$(C_1$-$C_{22})$ alkyl, $(C_1$-$C_{22})$ alkylamino-$(C_1$-$C_{22})$ alkylamino, $(C_1$-$C_{22})$ alkylamino-$(C_1$-$C_{22})$ alkylamino $(C_1$-$C_{22})$ alkylamino, $(C_1$-$C_{22})$ aminoalkylcarboxy, arylamino $(C_1$-$C_{22})$ alkyl, $(C_1$-$C_{22})$ aminoalkyloxy $(C_1$-$C_{22})$ aminoalkylaminocarbonyl, $(C_1$-$C_{22})$ aminoalkylaminocarbonyl, $(C_1$-$C_{22})$ aminoalkylcarboxyamido, $(C_1$-$C_{22})$ quaternary ammonium alkylcarboxy, di$(C_1$-$C_{22}$ alkyl) aminoalkyl, $H_2N$—$HC(Q_5)$-C(O)—O—, $H_2N$—$HC(Q_5)$-C(O)—N(H)—, $(C_1$-$C_{22})$ azidoalkyloxy, $(C_1$-$C_{22})$ cyanoalkyloxy, P.G.-HN—$HC(Q_5)$-C(O)—O—, $(C_1$-$C_{22})$ guanidinoalkyloxy, and $(C_1$-$C_{22})$ guanidinoalkylcarboxy.

In some embodiments, $R_1$ through $R_4$, $R_6$, $R_7$, $R_{11}$, $R_{12}$, $R_{15}$, $R_{16}$, and $R_{18}$ are independently selected from the group consisting of hydrogen, hydroxyl, $(C_1$-$C_{18})$ alkyl, $(C_1$-$C_{18})$ hydroxyalkyl, $(C_1$-$C_{18})$ alkyloxy-$(C_1$-$C_{18})$ alkyl, $(C_1$-$C_{18})$ alkylcarboxy-$(C_1$-$C_{18})$ alkyl, $(C_1$-$C_{18})$ alkylamino-$(C_1$-$C_{18})$ alkyl, $(C_1$-$C_{18})$ alkylamino-$(C_1$-$C_{18})$ alkylamino, $(C_1$-$C_{18})$ alkylamino-$(C_1$-$C_{18})$ alkylamino- $(C_1$-$C_{18})$ alkylamino, $(C_1$-$C_{18})$ aminoalkyl, aryl, arylamino-$(C_1$-$C_{18})$ alkyl, oxo, $(C_1$-$C_{18})$ aminoalkyloxy, $(C_1$-$C_{18})$ aminoalkyloxy-$(C_1$-$C_{18})$ alkyl, $(C_1$-$C_{18})$ aminoalkylcarboxy, $(C_1$-$C_{18})$ aminoalkylaminocarbonyl, $(C_1$-$C_{18})$ aminoalkyl-carboxamido, di$(C_1$-$C_{18}$ alkyl)aminoalkyl, $(C_1$-$C_{18})$ guanidinoalkyloxy, $(C_1$-$C_{18})$ quaternary ammonium alkylcarboxy, and $(C_1$-$C_{18})$ guanidinoalkyl carboxy; and $R_5$, $R_8$, $R_9$, $R_{10}$, $R_{13}$, $R_{14}$ and $R_{17}$ are independently deleted when one of rings A, B, C, or D is unsaturated so as to complete the valency of the carbon atom at that site, or $R_5$, $R_8$, $R_9$, $R_{10}$, $R_{13}$, and $R_{14}$ are independently selected from the group consisting of hydrogen, hydroxyl, $(C_1-C_{18})$ alkyl, $(C_1-C_{18})$ hydroxyalkyl, $(C_1-C_{18})$ alkyloxy-$(C_1-C_{18})$ alkyl, $(C_1-C_{18})$ alkylcarboxy-$(C_1-C_{18})$ alkyl, $(C_1-C_{18})$ alkylamino-$(C_1-C_{18})$alkyl, $(C_1-C_{18})$ alkylamino-$(C_1-C_{18})$ alkylamino, $(C_1-C_{18})$ alkylamino-$(C_1-C_{18})$ alkylamino- $(C_1-C_{18})$ alkylamino, $(C_1-C_{18})$ aminoalkyl, aryl, arylamino-$(C_1-C_{18})$ alkyl, oxo, $(C_1-C_{18})$ aminoalkyloxy, $(C_1-C_{18})$ aminoalkyloxy-$(C_1-C_{18})$ alkyl, $(C_1-C_{18})$ aminoalkylcarboxy, $(C_1-C_{18})$ aminoalkylaminocarbonyl, $(C_1-C_{18})$ aminoalkylcarboxamido, di$(C_1-C_{18}$ alkyl)aminoalkyl, $(C_1-C_{18})$ guanidinoalkyloxy, $(C_1-C_{18})$ quaternary ammonium alkylcarboxy, and $(C_1-C_{18})$ guanidinoalkyl carboxy, provided that at least two or three of $R_{1-4}$, $R_6$, $R_7$, $R_{11}$, $R_{12}$, $R_{15}$, $R_{16}$, $R_{17}$, and $R_{18}$ are independently selected from the group consisting of of hydrogen, hydroxyl, an unsubstituted $(C_1-C_{18})$ alkyl, unsubstituted $(C_1-C_{18})$ hydroxyalkyl, unsubstituted $(C_1-C_{18})$ alkyloxy-$(C_1-C_{18})$ alkyl, unsubstituted $(C_1-C_{18})$ alkylcarboxy-$(C_1-C_{18})$ alkyl, unsubstituted $(C_1-C_{18})$ alkylamino-$(C_1-C_{18})$alkyl, unsubstituted $(C_1-C_{18})$ alkylamino-$(C_1-C_{18})$ alkylamino, unsubstituted $(C_1-C_{18})$ alkylamino-$(C_1-C_{18})$ alkylamino- $(C_1-C_{18})$ alkylamino, an unsubstituted $(C_1-C_{18})$ aminoalkyl, an unsubstituted aryl, an unsubstituted arylamino-$(C_1-C_{18})$ alkyl, oxo, an unsubstituted $(C_1-C_{18})$ aminoalkyloxy, an unsubstituted $(C_1-C_{18})$ aminoalkyloxy-$(C_1-C_{18})$ alkyl, an unsubstituted $(C_1-C_{18})$ aminoalkylcarboxy, an unsubstituted $(C_1-C_{18})$ aminoalkylaminocarbonyl, an unsubstituted $(C_1-C_{18})$ aminoalkylcarboxamido, an unsubstituted di$(C_1-C_{18}$ alkyl)aminoalkyl, unsubstituted $(C_1-C_{18})$ guanidinoalkyloxy, unsubstituted $(C_1-C_{18})$ quaternary ammonium alkylcarboxy, and unsubstituted $(C_1-C_{18})$ guanidinoalkyl carboxy.

In some embodiments, $R_3$, $R_7$, $R_{12}$, and $R_{18}$ are independently selected from the F<group consisting of hydrogen, an unsubstituted $(C_1-C_{18})$ alkyl, unsubstituted $(C_1-C_{18})$ hydroxyalkyl, unsubstituted $(C_1-C_{18})$ alkyloxy-$(C_1-C_{18})$ alkyl, unsubstituted $(C_1-C_{18})$ alkylcarboxy-$(C_1-C_{18})$ alkyl, unsubstituted $(C_1-C_{18})$ alkylamino-$(C_1-C_{18})$alkyl, unsubstituted $(C_1-C_{18})$ alkylamino-$(C_1-C_{18})$ alkylamino, unsubstituted $(C_1-C_{18})$ alkylamino-$(C_1-C_{18})$ alkylamino- $(C_1-C_{18})$ alkylamino, an unsubstituted $(C_1-C_{18})$ aminoalkyl, an unsubstituted arylamino-$(C_1-C_{18})$ alkyl, an unsubstituted $(C_1-C_{18})$ aminoalkyloxy, an unsubstituted $(C_1-C_{18})$ aminoalkyloxy-$(C_1-C_{18})$ alkyl, an unsubstituted $(C_1-C_{18})$ aminoalkylcarboxy, an unsubstituted $(C_1-C_{18})$ aminoalkylaminocarbonyl, an unsubstituted $(C_1-C_{18})$ aminoalkylcarboxamido, an unsubstituted di$(C_1-C_{18}$ alkyl)aminoalkyl, unsubstituted $(C_1-C_{18})$ guanidinoalkyloxy, unsubstituted $(C_1-C_{18})$ quaternary ammonium alkylcarboxy, and unsubstituted $(C_1-C_{18})$ guanidinoalkyl carboxy.

In some embodiments, $R_1$, $R_2$, $R_4$, $R_5$, $R_6$, $R_8$, $R_9$, $R_{10}$, $R_{11}$, $R_{13}$, $R_{14}$, $R_{15}$, $R_{16}$, and $R_{17}$ are independently selected from the group consisting of hydrogen and unsubstituted $(C_1-C_6)$ alkyl.

In some embodiments, $R_3$, $R_7$, $R_{12}$, and $R_{18}$ are independently selected from the group consisting of hydrogen, an unsubstituted $(C_1-C_6)$ alkyl, unsubstituted $(C_1-C_6)$ hydroxyalkyl, unsubstituted $(C_1-C_{16})$ alkyloxy-$(C_1-C_5)$ alkyl, unsubstituted $(C_1-C_{16})$ alkylcarboxy-$(C_1-C_5)$ alkyl, unsubstituted $(C_1-C_{16})$ alkylamino-$(C_1-C_5)$alkyl, $(C_1-C_{16})$ alkylamino-$(C_1-C_5)$ alkylamino, unsubstituted $(C_1-C_{16})$ alkylamino-$(C_1-C_{16})$ alkylamino-$(C_1-C_5)$ alkylamino, an unsubstituted $(C_1-C_{16})$ aminoalkyl, an unsubstituted arylamino-$(C_1-C_5)$ alkyl, an unsubstituted $(C_1-C_5)$ aminoalkyloxy, an unsubstituted $(C_1-C_{16})$ aminoalkyloxy-$(C_1-C_5)$ alkyl, an unsubstituted $(C_1-C_5)$ aminoalkylcarboxy, an unsubstituted $(C_1-C_5)$ aminoalkylaminocarbonyl, an unsubstituted $(C_1-C_5)$ aminoalkylcarboxamido, an unsubstituted di$(C_1-C_5$ alkyl)amino-$(C_1-C_5)$ alkyl, unsubstituted $(C_1-C_5)$ guanidinoalkyloxy, unsubstituted $(C_1-C_{16})$ quaternary ammonium alkylcarboxy, and unsubstituted $(C_1-C_{16})$ guanidinoalkylcarboxy.

In some embodiments, $R_1$, $R_2$, $R_4$, $R_5$, $R_6$, $R_8$, $R_{10}$, $R_{11}$, $R_{14}$, $R_{16}$, and $R_{17}$ are each hydrogen; and $R_9$ and $R_{13}$ are each methyl.

In some embodiments, $R_3$, $R_7$, $R_{12}$, and $R_{18}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy; and $R_{18}$ is selected from the group consisting of alkylaminoalkyl; alkoxycarbonylalkyl; alkylcarbonyloxyalkyl; di(alkyl)aminoalkyl; alkylaminoalkyl; alkyoxycarbonylalkyl; alkylcarboxyalkyl; and hydroxyalkyl.

In some embodiments, $R_3$, $R_7$, and $R_{12}$ are the same.

In some embodiments, $R_3$, $R_7$, and $R_{12}$ are aminoalkyloxy.

In some embodiments, $R_{18}$ is alkylaminoalkyl.
In some embodiments, $R_{18}$ is alkoxycarbonylalkyl.
In some embodiments, $R_{18}$ is di(alkyl)aminoalkyl.
In some embodiments, $R_{18}$ is alkylcarboxyalkyl.
In some embodiments, $R_{18}$ is hydroxyalkyl.

In some embodiments, $R_3$, $R_7$, and $R_{12}$ are aminoalkylcarboxy.

In some embodiments, $R_3$, $R_7$, $R_{12}$, and $R_{18}$ are independently selected from the group consisting of aminoalkyloxy; aminoalkylcarboxy; alkylaminoalkyl; di-(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy, and wherein $R_{18}$ is selected from the group consisting of alkylaminoalkyl; di-(alkyl)aminoalkyl; alkoxycarbonylalkyl; and alkylcarboxyalkyl.

In some embodiments, $R_3$, $R_7$, and $R_{12}$ are independently selected from the group consisting of aminoalkyloxy and aminoalkylcarboxy, and wherein $R_{18}$ is selected from the group consisting of alkylaminoalkyl; di-(alkyl)aminoalkyl; and alkoxycarbonylalkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; $C_{10}$-alkoxy-carbonyl-$C_4$-alkyl; $C_6$-alkyl-carboxy-$C_4$-alkyl; $C_8$-alkyl-carboxy-$C_4$-alkyl; and $C_{10}$-alkyl-carboxy-$C_4$-alkyl.

In some embodiments, $R_3$, $R_7$, $R_{12}$, and $R_{18}$ are independently selected from the group consisting of amino-$C_3$-alkyloxy; amino-$C_3$-alkyl-carboxy; $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; and $C_{10}$-alkoxy-carbonyl-$C_4$-alkyl.

In some embodiments, $R_3$, $R_7$, and $R_{12}$, are independently selected from the group consisting of amino-$C_3$-alkyloxy or amino-$C_3$-alkyl-carboxy, and wherein $R_{18}$ is selected from the group consisting of $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; $C_{13}$-alkylamino-$C$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; $C_{10}$- alkoxy-carbonyl-$C_4$-alkyl; $C_6$-alkyl-carboxy-$C_4$-alkyl; $C_8$-alkyl-carboxy-$C_4$-alkyl; and $C_{10}$-alkyl-carboxy-$C_4$-alkyl.

In some embodiments, $R_3$, $R_7$, and $R_{12}$ are independently selected from the group consisting of amino-$C_3$-alkyloxy or amino-$C_3$-alkyl-carboxy, and wherein $R_{18}$ is selected from the group consisting of $C_8$-alkylamino-$C_5$-alkyl; $C_{12}$-alkylamino-$C_5$-alkyl; $C_{13}$-alkylamino-$C_5$-alkyl; $C_{16}$-alkylamino-$C_5$-alkyl; di-($C_5$-alkyl)amino-$C_5$-alkyl; $C_6$-alkoxy-carbonyl-$C_4$-alkyl; $C_8$-alkoxy-carbonyl-$C_4$-alkyl; and $C_{10}$-alkoxy-carbonyl-$C_4$-alkyl.

In some embodiments, $R_3$, $R_7$, $R_{12}$, and $R_{18}$ are independently selected from the group consisting of amino-$C_3$-alkyloxy; amino-$C_3$-alkyl-carboxy; amino-$C_2$-alkylcarboxy; $C_8$-alkylamino-$C_5$-alkyl; $C_8$-alkoxy-carbonyl-$C_4$-alkyl; $C_{10}$-alkoxy-carbonyl-$C_4$-alkyl; $C_8$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; $C_{16}$-alkylamino-$C_5$-alkyl; $C_{12}$-alkylamino-$C_5$-alkyl; and hydroxy($C_5$)alkyl.

In some embodiments, $R_{18}$ is selected from the group consisting of $C_8$-alkylamino-$C_5$-alkyl or $C_8$-alkoxy-carbonyl-$C_4$-alkyl.

In some embodiments, at least $R_{18}$ can have the following structure:

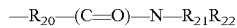

—$R_{20}$—(C=O)—N—$R_{21}R_{22}$ wherein $R_{20}$ is omitted or alkyl, alkenyl, alkynyl, or aryl, and $R_{21}$ and $R_{22}$ are independently selected from the group consisting of hydrogen, alkyl, alkenyl, alkynyl, or aryl, provided that at least one of $R_{21}$ and $R_{22}$ is not hydrogen.

In some embodiments, $R_{21}$ and $R_{22}$ are independently selected from the group consisting of hydrogen, $C_1$-$C_{24}$ alkyl, $C_2$-$C_{24}$ alkenyl, $C_2$-$C_{24}$ alkynyl, $C_6$ or $C_{10}$ aryl, 5 to 10 membered heteroaryl, 5 to 10 membered heterocyclyl, $C_{7-13}$ aralkyl, (5 to 10 membered heteroaryl)-$C_1$-$C_6$ alkyl, $C_{3-10}$ carbocyclyl, $C_{4-10}$ (carbocyclyl)alkyl, (5 to 10 membered heterocyclyl)-$C_1$-$C_6$ alkyl, amido, and a suitable amine protecting group, provided that at least one of $R_{21}$ and $R_{22}$ is not hydrogen. In some embodiments, $R_{21}$ and $R_{22}$, together with the atoms to which they are attached, form a 5 to 10 membered heterocyclyl ring.

In some embodiments, one or more of rings A, B, C, and D is heterocyclic.

In some embodiments, rings A, B, C, and D are non-heterocyclic.

In some embodiments, the CSA compound is a compound of Formula IV, which is a subset of Formula III, or salt thereof, having a steroidal backbone:

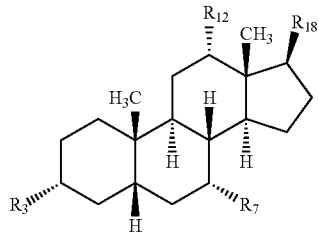

(IV)

In some embodiments, $R_3$, $R_7$, and $R_{12}$ are independently selected from the group consisting of hydrogen, an unsubstituted ($C_1$-$C_{22}$) alkyl, unsubstituted ($C_1$-$C_{22}$) hydroxyalkyl, unsubstituted ($C_1$-$C_{22}$) alkyloxy-($C_1$-$C_{22}$) alkyl, unsubstituted ($C_1$-$C_{22}$) alkylcarboxy-($C_1$-$C_{22}$) alkyl, unsubstituted ($C_1$-$C_{22}$) alkylamino-($C_1$-$C_{22}$)alkyl, unsubstituted ($C_1$-$C_{22}$) alkylamino-($C_1$-$C_{22}$) alkylamino, unsubstituted ($C_1$-$C_{22}$) alkylamino-($C_1$-$C_{22}$) alkylamino-($C_1$-$C_{18}$) alkylamino, an unsubstituted ($C_1$-$C_{22}$) aminoalkyl, an unsubstituted arylamino-($C_1$-$C_{22}$) alkyl, an unsubstituted ($C_1$-$C_{22}$) aminoalkyloxy, an unsubstituted ($C_1$-$C_{22}$) aminoalkyloxy-($C_1$-$C_{22}$) alkyl, an unsubstituted ($C_1$-$C_{22}$) aminoalkylcarboxy, an unsubstituted ($C_1$-$C_{22}$) aminoalkyl-aminocarbonyl, an unsubstituted ($C_1$-$C_{22}$) aminoalkylcarboxamido, an unsubstituted di($C_1$-$C_{22}$ alkyl)aminoalkyl, unsubstituted ($C_1$-$C_{22}$) guanidinoalkyloxy, unsubstituted ($C_1$-$C_{22}$) quaternary ammonium alkylcarboxy, and unsubstituted ($C_1$-$C_{22}$) guanidinoalkyl carboxy.

In some embodiments, $R_3$, $R_7$, and $R_{12}$ are independently selected from the group consisting of hydrogen, an unsubstituted ($C_1$-$C_6$) alkyl, unsubstituted ($C_1$-$C_6$) hydroxyalkyl, unsubstituted ($C_1$-$C_{16}$) alkyloxy-($C_1$-$C_5$) alkyl, unsubstituted ($C_1$-$C_{16}$) alkylcarboxy-($C_1$-$C_5$) alkyl, unsubstituted ($C_1$-$C_{16}$) alkylamino-($C_1$-$C_5$)alkyl, unsubstituted ($C_1$-$C_{16}$) alkylamino-($C_1$-$C_5$) alkylamino, unsubstituted ($C_1$-$C_{16}$) alkylamino-($C_1$-$C_{16}$) alkylamino-($C_1$-$C_5$) alkylamino, an unsubstituted ($C_1$-$C_{16}$) aminoalkyl, an unsubstituted arylamino-($C_1$-$C_5$) alkyl, an unsubstituted ($C_1$-$C_5$) aminoalkyloxy, an unsubstituted ($C_1$-$C_{16}$) aminoalkyloxy-($C_1$-$C_5$) alkyl, an unsubstituted ($C_1$-$C_5$) aminoalkylcarboxy, an unsubstituted ($C_1$-$C_5$) aminoalkylaminocarbonyl, an unsubstituted ($C_1$-$C_5$) aminoalkylcarboxamido, an unsubstituted di($C_1$-$C_5$ alkyl)amino-($C_1$-$C_5$) alkyl, unsubstituted ($C_1$-$C_5$) guanidinoalkyloxy, unsubstituted ($C_1$-$C_{16}$) quaternary ammonium alkylcarboxy, and unsubstituted ($C_1$-$C_{16}$) guanidinoalkylcarboxy.

In some embodiments, $R_3$, $R_7$, and $R_{12}$ are independently selected from the group consisting of aminoalkyloxy; aminoalkylcarboxy; alkylaminoalkyl; alkoxycarbonylalkyl; alkylcarbonylalkyl; di(alkyl)aminoalkyl; alkylcarboxyalkyl; and hydroxyalkyl.

In some embodiments, $R_3$, $R_7$, and $R_{12}$ are independently selected from the group consisting of aminoalkyloxy and aminoalkylcarboxy.

In some embodiments, $R_3$, $R_7$, and $R_{12}$ are the same. In some embodiments, $R_3$, $R_7$, and $R_{12}$ are aminoalkyloxy. In some embodiments, $R_3$, $R_7$, and $R_{12}$ are aminoalkylcarboxy.

In some embodiments, $R_3$, $R_7$, and $R_{12}$ are independently selected from the group consisting of amino-$C_3$-alkyloxy; amino-$C_3$-alkyl-carboxy; $C_8$-alkylamino-$C_5$-alkyl; $C_8$-alkoxy-carbonyl-$C_4$-alkyl; $C_5$-alkyl-carbonyl-$C_4$-alkyl; di-($C_5$-alkyl)amino-$C_5$-alkyl; $C_{13}$-alkylamino-$C_5$-alkyl; $C_6$-alkoxy-carbonyl-$C_4$-alkyl; $C_6$-alkyl-carboxy-$C_4$-alkyl; and $C_{16}$-alkylamino-$C_5$-alkyl.

In some embodiments, CSA compounds as disclosed herein can be a compound of Formula I, Formula II, Formula III, Formula IV, or salts thereof wherein at least $R_{18}$ of the steroidal backbone includes amide functionality in which the carbonyl group of the amide is positioned between the amido nitrogen of the amide and fused ring D of the steroidal backbone. For example, any of the embodiments described above can substitute $R_{18}$ for an $R_{18}$ including amide functionality in which the carbonyl group of the amide is positioned between the amido nitrogen of the amide and fused ring D of the steroidal backbone.

In some embodiments, one or more of $R_3$, $R_7$, or $R_{12}$ may include a guanidine group as a cationic functional group and may be bonded to the steroid backbone by an ether linkage. For example, one or more of $R_3$, $R_7$, or $R_{12}$ may be a guanidinoalkyloxy group. An example includes $H_2N$—C(=NH)—NH-alkyl-O—,

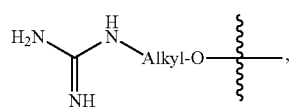

wherein the alkyl portion is defined as with the embodiments described above. In a preferred embodiment, the alkyl portion is a straight chain with 3 carbon atoms, and therefore one or more of $R_3$, $R_7$, or $R_{12}$ may be a guanidinopropyloxy group.

One of skill in the art will recognize that other cationic functional groups may be utilized, and that the cationic functional groups may be bonded to the steroid backbone through a variety of other tethers or linkages. For example, the cationic functional groups may be bonded to the steroid backbone by an ester linkage. For example, one or more of $R_3$, $R_7$, or $R_{12}$ may be an aminoalkylcarboxy or guanidinoalkylcarboxy, such as $H_2N$-alkyl-C(=O)—O— or $H_2N$—C(=NH)—NH-alkyl-C(=O)—O—, wherein the alkyl portion is defined as with the embodiments described above. In other embodiments, the cationic functional groups may be bonded to the steroid backbone by an amide linkage. For example, one or more of $R_3$, $R_7$, or $R_{12}$ may be an aminoalkylcarbonylamino (i.e. aminoalkylcarboxamido) or guanidinoalkyl-carbonylamino (i.e. guanidinoalkylcarboxamido), such as $H_2N$-alkyl-C(=O)—NH— or $H_2N$—C(=NH)—NH-alkyl-C(=O)—NH—, wherein the alkyl portion is defined as with the embodiments described above.

Additionally, one of skill in the art will recognize that the tethers may be of varying lengths. For example, the length between the steroid backbone and the cationic functional group (e.g., amino or guanidino group), may be between 1 and 15 atoms or even more than 15 atoms. In other embodiments, the length may be between 1 and 8 atoms. In a preferred embodiment, the length of the tether is between two and four atoms. In other embodiments, there is no tether, such that the cationic functional group is bonded directly to the steroid backbone.

One of skill in the art will also note that the various cationic functional groups of the present disclosure may be utilized in combination, such that one or more of $R_3$, $R_7$, or $R_{12}$ may include one variation of cationic functional group while one or more of another of $R_3$, $R_7$, or $R_{12}$ of the same compound may include a different variation of cationic functional group. Alternatively, two or more of $R_3$, $R_7$, or $R_{12}$ may include the same cationic functional group, or all of $R_3$, $R_7$, or $R_{12}$ may include the same cationic functional group (in embodiments where all of $R_3$, $R_7$, or $R_{12}$ are cationic functional groups).

Additionally, although in a preferred embodiment one or more cationic functional groups are disposed at $R_3$, $R_7$, or $R_{12}$, one of skill in the art will recognize that in other embodiments, $R_3$, $R_7$, or $R_{12}$ may not be cationic functional groups and/or one or more cationic functional groups may be disposed at other locations of the steroid backbone. For example, one or more cationic functional groups may be disposed at $R_1$, $R_2$, $R_3$, $R_4$, $R_6$, $R_7$, $R_{11}$, $R_{12}$, $R_{15}$, $R_{16}$, $R_{17}$, and/or $R_{18}$.

The compounds and compositions disclosed herein are optionally prepared as salts. The term "salt" as used herein is a broad term, and is to be given its ordinary and customary meaning to a skilled artisan (and is not to be limited to a special or customized meaning), and refers without limitation to a salt of a compound. In some embodiments, the salt is an acid addition salt of the compound. Salts can be obtained by reacting a compound with inorganic acids such as hydrohalic acid (e.g., hydrochloric acid or hydrobromic acid), sulfuric acid, nitric acid, and phosphoric acid. Salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, naphthalenesulfonic acid, or naphthalenedisulfonic acid (NDSA). Salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the salt is a hydrochloride salt. In some embodiments, the salt is a mono-hydrochloride salt, a di-hydrochloride salt, a tri-hydrochloride salt, or a tetra-hydrochloride salt. Additional examples of salts include sulfuric acid addition salts, sulfonic acid addition salts, disulfonic acid addition salts, 1,5-naphthalenedisulfonic acid addition salts, sulfate salts, and bisulfate salts.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A dermal filler composition for syringe-injection into dermal tissue as a soft tissue filler to cosmetically and/or functionally increase the size and/or modify the shape of a body part, comprising:
  a biologically compatible dermal filler material in the form of a liquid, gel, paste, or viscous material so as to be syringe-injectable into dermal tissue, wherein the dermal filler material is a soft tissue filler that cosmetically and/or functionally increases the size and/or modifies the shape of a body part when syringe-injected therein; and
  one or more cationic steroidal antimicrobial (CSA) compounds incorporated into the biologically compatible dermal filler material so that, when injected into soft tissue, the dermal filler composition can form a bolus having a reservoir of CSA compounds incorporated into and distributed within a matrix of the dermal filler composition and provide effective time release of the one or more CSA compounds from the dermal filler material.

2. The dermal filler composition of claim 1, wherein the dermal filler material comprises one or more syringe-injectable materials that cosmetically and/or functionally increase the size and/or modify the shape of a body part selected from lip, breast, buttock, chest, and calf.

3. The dermal filler composition of claim 1, wherein the dermal filler material comprises syringe-injectable hyaluronic acid formulated for use in at least one of genital augmentation, plastic surgery, or labiaplasty.

4. The dermal filler composition of claim 1, wherein the dermal filler material comprises syringe-injectable collagen formulated for use in at least one of genital augmentation, plastic surgery, or labiaplasty.

5. The dermal filler composition of claim 1, wherein the dermal filler material comprises a syringe-injectable material selected from hydroxyapatite mineral, poly-l-lactic acid, silicone, and polymethylmethacrylate.

6. The dermal filler composition of claim 1, wherein the dermal filler material comprises syringe-injectable botox and wherein the one or more cationic CSA compounds increase the rate of tissue healing than syringe-injectable botox that does not incorporate the one or more CSA compounds.

7. The dermal filler composition of claim 1, wherein the one or more CSA compounds are included in the dermal filler composition in an amount ranging from about 0.1% to about 30% (w/w).

8. The dermal filler composition of claim 1, wherein the one or more CSA compounds provide anti-microbial activity, anti-inflammatory activity, and increased rate of tissue wound healing than a dermal filler that does not incorporate the one or more CSA compounds.

9. The dermal filler composition of claim 1, wherein the one or more CSA compounds includes CSA-131.

10. The dermal filler composition of claim 1, wherein the one or more CSA compounds includes one or more sulfonic acid addition salts.

11. The dermal filler composition of claim 10, wherein the one or more sulfonic acid addition salts includes 1,5-naphthalenedisulfonic acid salt.

12. The dermal filler composition of claim 1, wherein the dermal filler composition provides enhanced protection against biofouling, biofilm formation, and infection than a dermal filler that does not incorporate the one or more CSA compounds.

13. The dermal filler composition of claim 1, wherein the dermal filler composition provides enhanced anti-inflammatory activity and reduced pain and swelling than a dermal filler that does not incorporate the one or more CSA compounds.

14. A method for cosmetically or functionally increasing the size and/or modifying the shape of a patient's body part and controlling microbial growth at a dermal treatment site of the patient's body part, comprising:
    providing a syringe-injectable dermal filler composition comprising a biologically compatible dermal filler material and one or more cationic steroidal antimicrobial (CSA) compounds;
    injecting via syringe-delivery the treatment composition into dermal tissue at the dermal treatment site of the patient's body part; and
    the dermal filler composition cosmetically or functionally increasing the size and/or modifying the shape of the patient's body part and forming a bolus having a reservoir of CSA compounds that are effective in killing one or more microbes contacting the treatment composition.

15. The method of claim 14, wherein the one or more CSA compounds includes CSA-131, and wherein the CSA-131 is provided as an acid addition salt of 1,5-naphthalenedisulfonic acid.

16. The method of claim 14, wherein the dermal filler composition cosmetically or functionally increases the size and/or modifies the shape of a body part selected from lip, breast, buttock, chest, genital, and calf.

17. The method of claim 14, wherein the dermal filler composition cosmetically or functionally increases the size and/or modifies the shape of a body part in a procedure selected from genital augmentation, plastic surgery, and labiaplasty.

18. The method of claim 14, wherein the one or more CSA compounds provide enhanced anti-microbial activity, enhanced anti-inflammatory activity, increased rate of tissue wound healing, and reduced pain and swelling than a dermal filler that does not incorporate the one or more CSA compounds.

19. The method of claim 14, wherein the dermal filler composition provides enhanced anti-inflammatory activity and reduced pain and swelling than a dermal filler that does not incorporate the one or more CSA compounds.

20. A dermal filler composition for syringe-injection into dermal tissue, comprising:
    a biologically compatible dermal filler material in the form of a syringe-injectable liquid, gel, paste, or viscous material that is syringe-injectable into dermal tissue to cosmetically and/or functionally increase the size and/or modify the shape of a body part when syringe-injected therein; and
    one or more cationic steroidal antimicrobial (CSA) compounds incorporated into the biologically compatible dermal filler material so that, when injected into soft tissue, the dermal filler composition can form a bolus having a reservoir of CSA compounds incorporated into and distributed within a matrix of the dermal filler composition and provide effective time release of the one or more CSA compounds from the dermal filler material, wherein the one or more CSA compounds includes one or more sulfonic acid addition salts and wherein the one or more sulfonic acid addition salts includes 1,5-naphthalenedisulfonic acid salt.

* * * * *

UNITED STATES PATENT AND TRADEMARK OFFICE
CERTIFICATE OF CORRECTION

| | |
|---|---|
| PATENT NO. | : 11,253,634 B2 |
| APPLICATION NO. | : 16/184211 |
| DATED | : February 22, 2022 |
| INVENTOR(S) | : Paul B. Savage et al. |

It is certified that error appears in the above-identified patent and that said Letters Patent is hereby corrected as shown below:

In the Specification

Column 2
Line 33, change "some embodiments" to – in some embodiments –

Column 3
Line 12, change "significantly sensitivity" to – significant sensitivity –

Column 5
Line 25, change "show n" to – shown –

Column 10
Line 32, change "includes" to – include –

Signed and Sealed this
Second Day of August, 2022

Katherine Kelly Vidal
*Director of the United States Patent and Trademark Office*